United States Patent
Quadri et al.

(10) Patent No.: US 10,610,362 B2
(45) Date of Patent: Apr. 7, 2020

(54) REPLACEMENT HEART VALVES, DELIVERY DEVICES AND METHODS

(71) Applicant: Edwards Lifesciences CardiAQ LLC, Irvine, CA (US)

(72) Inventors: Arshad Quadri, West Hartford, CT (US); J. Brent Ratz, Winchester, MA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 241 days.

(21) Appl. No.: 15/961,353

(22) Filed: Apr. 24, 2018

(65) Prior Publication Data

US 2018/0235756 A1 Aug. 23, 2018

Related U.S. Application Data

(63) Continuation of application No. 14/702,233, filed on May 1, 2015, now Pat. No. 9,949,827, which is a (Continued)

(51) Int. Cl.
*A61F 2/24* (2006.01)

(52) U.S. Cl.
CPC .......... *A61F 2/2427* (2013.01); *A61F 2/2418* (2013.01); *A61F 2/2436* (2013.01);
(Continued)

(58) Field of Classification Search
CPC ........ A61F 2/24; A61F 2/2418; A61F 2/2427; A61F 2/2436; A61F 2220/0008;
(Continued)

(56) References Cited

U.S. PATENT DOCUMENTS

| | | | |
|---|---|---|---|
| 3,657,744 | A | 4/1972 | Ersek |
| 3,671,979 | A | 6/1972 | Moulopoulos |

(Continued)

FOREIGN PATENT DOCUMENTS

| | | |
|---|---|---|
| CA | 2304325 A1 | 10/2000 |
| DE | 102006052564 B3 | 12/2007 |

(Continued)

OTHER PUBLICATIONS

Bavaria, Joseph E. M.D. et al.: "Transcatheter Mitral Valve Implantation: The Future Gold Standard for MR?," Applicant requests the Examiner to consider this reference to be prior art as of Dec. 2010.
(Continued)

*Primary Examiner* — Kathleen S Holwerda
(74) *Attorney, Agent, or Firm* — Klarquist Sparkman, LLC; Joel B. German

(57) ABSTRACT

A replacement heart valve and method of treating valve insufficiency includes an expandable frame configured to engage a native valve annulus. A valve body is coupled to the frame. The valve body can include a leaflet portion and possibly a skirt portion. A portion of the frame has a foreshortening portion configured to longitudinally expand when urged to a radially compacted state and longitudinally contract when urged to a radially expanded state. In one embodiment the valve skirt is attached to the frame so that it can adapt to changes in the length of the frame. A delivery device in some embodiments can use one or more coverings, such as sheaths, to controllably release the replacement heart valve at a native heart valve.

20 Claims, 19 Drawing Sheets

Related U.S. Application Data continuation of application No. 13/756,424, filed on Jan. 31, 2013, now Pat. No. 9,023,100, which is a continuation of application No. 13/244,080, filed on Sep. 23, 2011, now Pat. No. 8,652,203.

(60) Provisional application No. 61/385,651, filed on Sep. 23, 2010.

(52) U.S. Cl.
CPC ........... *A61F 2220/0008* (2013.01); *A61F 2220/0041* (2013.01); *A61F 2220/0066* (2013.01); *A61F 2220/0075* (2013.01); *A61F 2230/008* (2013.01); *A61F 2230/0054* (2013.01)

(58) Field of Classification Search
CPC ...... A61F 2220/0041; A61F 2220/0066; A61F 2220/0075; A61F 2/07–2002/077; A61F 2/82–2/97
USPC .............................................. 623/2.11–2.42
See application file for complete search history.

(56) References Cited

U.S. PATENT DOCUMENTS

| | | |
|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,655,771 A | 4/1987 | Wallsten |
| 4,733,665 A | 3/1988 | Palmaz |
| 4,776,337 A | 10/1988 | Palmaz |
| 4,777,951 A | 10/1988 | Cribier et al. |
| 4,865,600 A | 9/1989 | Carpentier et al. |
| 4,994,077 A | 2/1991 | Dobben |
| 5,197,978 A | 3/1993 | Hess |
| 5,326,371 A | 7/1994 | Love et al. |
| 5,332,402 A | 7/1994 | Teitelbaum |
| 5,370,685 A | 12/1994 | Stevens |
| 5,397,355 A | 3/1995 | Marin et al. |
| 5,411,552 A | 5/1995 | Andersen et al. |
| 5,415,667 A | 5/1995 | Frater |
| 5,439,446 A | 8/1995 | Barry |
| 5,474,563 A | 12/1995 | Myler et al. |
| 5,554,185 A | 9/1996 | Block et al. |
| 5,575,818 A | 11/1996 | Pinchuk |
| 5,607,444 A | 3/1997 | Lam |
| 5,669,919 A | 9/1997 | Sanders et al. |
| 5,693,061 A | 12/1997 | Pierce et al. |
| 5,697,382 A | 12/1997 | Love et al. |
| D390,957 S | 2/1998 | Fontaine |
| 5,725,519 A | 3/1998 | Penner et al. |
| 5,769,812 A | 6/1998 | Stevens et al. |
| 5,807,398 A | 9/1998 | Shaknovich |
| 5,810,873 A | 9/1998 | Morales |
| 5,855,601 A | 1/1999 | Bessler et al. |
| 5,868,782 A | 2/1999 | Frantzen |
| 5,879,381 A | 3/1999 | Moriuchi et al. |
| 5,902,334 A | 5/1999 | Dwyer et al. |
| 5,935,108 A | 8/1999 | Katoh et al. |
| 5,957,949 A | 9/1999 | Leonhardt et al. |
| 5,992,000 A | 11/1999 | Humphrey et al. |
| 6,004,328 A | 12/1999 | Solar |
| 6,015,431 A | 1/2000 | Thornton et al. |
| 6,042,606 A | 3/2000 | Frantzen |
| 6,053,940 A | 4/2000 | Wijay |
| 6,113,612 A | 9/2000 | Swanson et al. |
| 6,113,631 A | 9/2000 | Jansen |
| 6,123,722 A * | 9/2000 | Fogarty ............... A61F 2/07 623/1.1 |
| 6,132,458 A | 10/2000 | Staehle et al. |
| 6,152,937 A | 11/2000 | Peterson et al. |
| 6,159,237 A | 12/2000 | Alt et al. |
| 6,168,616 B1 | 1/2001 | Brown, III |
| 6,251,093 B1 | 6/2001 | Valley et al. |
| 6,280,466 B1 | 8/2001 | Kugler et al. |
| 6,306,141 B1 | 10/2001 | Jervis |
| 6,312,465 B1 | 11/2001 | Griffin et al. |
| 6,336,938 B1 | 1/2002 | Kavteladze et al. |
| 6,352,543 B1 | 3/2002 | Cole |
| 6,358,277 B1 | 3/2002 | Duran |
| 6,440,164 B1 | 8/2002 | DiMatteo et al. |
| 6,458,153 B1 | 10/2002 | Bailey et al. |
| 6,475,237 B2 | 11/2002 | Drasler et al. |
| 6,482,228 B1 | 11/2002 | Norred |
| 6,511,491 B2 | 1/2003 | Grudem et al. |
| 6,527,800 B1 | 3/2003 | McGuckin, Jr. et al. |
| 6,602,281 B1 | 8/2003 | Klein |
| 6,610,088 B1 | 8/2003 | Gabbay |
| 6,623,518 B2 | 9/2003 | Thompson et al. |
| 6,629,534 B1 | 10/2003 | St. Goar et al. |
| 6,641,606 B2 | 11/2003 | Ouriel et al. |
| D484,979 S | 1/2004 | Fontaine |
| 6,676,698 B2 | 1/2004 | McGuckin, Jr. et al. |
| 6,682,537 B2 | 1/2004 | Ouriel et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,746,422 B1 | 6/2004 | Noriega et al. |
| 6,749,560 B1 | 6/2004 | Konstorum et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,858,034 B1 | 2/2005 | Hijlkema et al. |
| 6,875,231 B2 | 4/2005 | Anduiza et al. |
| 6,893,460 B2 | 5/2005 | Spenser et al. |
| 6,908,481 B2 | 6/2005 | Cribier |
| 6,926,732 B2 | 8/2005 | Derus et al. |
| 6,929,660 B1 | 8/2005 | Ainsworth et al. |
| 6,936,058 B2 | 8/2005 | Forde et al. |
| 7,018,401 B1 | 3/2006 | Hyodoh et al. |
| 7,018,406 B2 | 3/2006 | Seguin et al. |
| 7,044,962 B2 | 5/2006 | Elliott |
| 7,087,088 B2 | 8/2006 | Berg et al. |
| 7,147,660 B2 | 12/2006 | Chobotov et al. |
| 7,147,661 B2 | 12/2006 | Chobotov et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| D553,747 S | 10/2007 | Fliedner |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,553,324 B2 | 6/2009 | Andreas et al. |
| 7,569,071 B2 | 8/2009 | Haverkost et al. |
| 7,585,321 B2 | 9/2009 | Cribier |
| 7,608,114 B2 | 10/2009 | Levine et al. |
| 7,615,072 B2 | 11/2009 | Rust et al. |
| 7,621,948 B2 | 11/2009 | Herrmann et al. |
| 7,748,389 B2 | 7/2010 | Salahieh et al. |
| 7,753,949 B2 | 7/2010 | Lamphere et al. |
| D622,387 S | 8/2010 | Igaki |
| D622,388 S | 8/2010 | Igaki |
| 7,771,463 B2 | 8/2010 | Ton et al. |
| 7,785,360 B2 | 8/2010 | Freitag |
| 7,803,185 B2 | 9/2010 | Gabbay |

(56) References Cited

U.S. PATENT DOCUMENTS

| | | |
|---|---|---|
| 7,806,917 B2 | 10/2010 | Xiao |
| 7,806,919 B2 | 10/2010 | Bloom et al. |
| 7,815,589 B2 | 10/2010 | Meade et al. |
| 7,815,673 B2 | 10/2010 | Bloom et al. |
| 7,824,443 B2 | 11/2010 | Salahieh et al. |
| 7,892,281 B2 | 2/2011 | Seguin et al. |
| D635,261 S | 3/2011 | Rossi |
| D635,262 S | 3/2011 | Rossi |
| 7,905,830 B2 | 3/2011 | Stefanchik et al. |
| 7,914,569 B2 | 3/2011 | Nguyen et al. |
| 7,981,151 B2 | 7/2011 | Rowe |
| 7,993,392 B2 | 8/2011 | Righini et al. |
| 8,016,877 B2 | 9/2011 | Seguin et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,109,996 B2 | 2/2012 | Stacchino et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,926 B2 | 5/2012 | Hartley et al. |
| 8,167,934 B2 | 5/2012 | Styrc et al. |
| 8,177,799 B2 | 5/2012 | Orban, III |
| 8,182,528 B2 | 5/2012 | Salahieh et al. |
| 8,182,530 B2 | 5/2012 | Huber |
| 8,197,528 B2 | 6/2012 | Colgan et al. |
| 8,216,261 B2 | 7/2012 | Solem |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,482 B2 | 7/2012 | Cottone et al. |
| D665,079 S | 8/2012 | Zago |
| D665,080 S | 8/2012 | Zago |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,052 B2 | 8/2012 | Salahieh et al. |
| 8,303,653 B2 | 11/2012 | Bonhoeffer et al. |
| 8,313,525 B2 | 11/2012 | Tuval et al. |
| 8,317,854 B1 | 11/2012 | Ryan et al. |
| 8,323,335 B2 | 12/2012 | Rowe et al. |
| 8,353,953 B2 | 1/2013 | Giannetti et al. |
| 8,361,137 B2 | 1/2013 | Perouse |
| 8,403,983 B2 | 3/2013 | Quadri et al. |
| 8,414,645 B2 | 4/2013 | Dwork et al. |
| 8,444,689 B2 | 5/2013 | Zhang |
| 8,449,599 B2 | 5/2013 | Chau et al. |
| 8,449,625 B2 | 5/2013 | Campbell et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,535,368 B2 | 9/2013 | Headley, Jr. et al. |
| 8,562,663 B2 | 10/2013 | Mearns et al. |
| 8,579,963 B2 | 11/2013 | Tabor |
| 8,579,964 B2 | 11/2013 | Lane et al. |
| 8,584,849 B2 | 11/2013 | McCaffrey |
| 8,585,749 B2 | 11/2013 | Shelso |
| 8,617,236 B2 | 12/2013 | Paul et al. |
| 8,640,521 B2 | 2/2014 | Righini et al. |
| 8,652,201 B2 | 2/2014 | Oberti et al. |
| 8,652,202 B2 | 2/2014 | Alon et al. |
| 8,672,992 B2 | 3/2014 | Orr |
| 8,679,174 B2 | 3/2014 | Ottma et al. |
| 8,679,404 B2 | 3/2014 | Liburd et al. |
| 8,707,957 B2 | 4/2014 | Callister et al. |
| 8,721,707 B2 | 5/2014 | Boucher et al. |
| 8,721,708 B2 | 5/2014 | Seguin et al. |
| 8,721,714 B2 | 5/2014 | Kelley |
| 8,728,154 B2 | 5/2014 | Alkhatib |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,753,384 B2 | 6/2014 | Leanna |
| 8,771,344 B2 | 7/2014 | Tran et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,852,267 B2 | 10/2014 | Cattaneo |
| 8,858,620 B2 | 10/2014 | Salahieh et al. |
| 8,870,950 B2 | 10/2014 | Hacohen |
| 8,876,883 B2 | 11/2014 | Rust |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,939,960 B2 | 1/2015 | Rosenman et al. |
| 8,961,583 B2 | 2/2015 | Hojeibane et al. |
| 8,961,593 B2 | 2/2015 | Bonhoeffer et al. |
| 8,974,524 B2 | 3/2015 | Yeung et al. |
| 8,998,979 B2 | 4/2015 | Seguin et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,524 B2 | 4/2015 | Eberhardt |
| 9,028,545 B2 | 5/2015 | Taylor |
| 9,029,418 B2 | 5/2015 | Dove et al. |
| 9,078,751 B2 | 7/2015 | Naor |
| 9,173,737 B2 | 11/2015 | Hill et al. |
| 9,180,004 B2 | 11/2015 | Alkhatib |
| 9,277,990 B2 | 3/2016 | Klima et al. |
| 9,277,993 B2 | 3/2016 | Gamarra et al. |
| 9,295,551 B2 | 3/2016 | Straubinger et al. |
| 9,326,815 B2 | 5/2016 | Watson |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,700,329 B2 | 7/2017 | Metzger et al. |
| 9,700,411 B2 | 7/2017 | Klima et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 2001/0007956 A1 | 7/2001 | Letac et al. |
| 2001/0047200 A1 | 11/2001 | White et al. |
| 2002/0016623 A1 | 2/2002 | Kula et al. |
| 2002/0032481 A1* | 3/2002 | Gabbay ............... A61F 2/2418 623/2.11 |
| 2002/0045929 A1 | 4/2002 | Diaz |
| 2002/0052644 A1 | 5/2002 | Shaolian et al. |
| 2002/0111619 A1 | 8/2002 | Keast et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0117009 A1 | 6/2004 | Cali et al. |
| 2004/0133273 A1 | 7/2004 | Cox |
| 2004/0210304 A1 | 10/2004 | Seguin et al. |

(56) References Cited

U.S. PATENT DOCUMENTS

| | | |
|---|---|---|
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0243230 A1 | 12/2004 | Navia et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2006/0020247 A1 | 1/2006 | Kagan et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0116625 A1 | 6/2006 | Renati et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0224232 A1 | 10/2006 | Chobotov |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0219620 A1 | 9/2007 | Eells et al. |
| 2007/0250151 A1 | 10/2007 | Pereira |
| 2007/0255394 A1 | 11/2007 | Ryan |
| 2007/0293940 A1 | 12/2007 | Schaeffer et al. |
| 2008/0009934 A1 | 1/2008 | Schneider et al. |
| 2008/0021546 A1 | 1/2008 | Patz et al. |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097571 A1 | 4/2008 | Denison et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2008/0262590 A1 | 10/2008 | Murray |
| 2009/0005863 A1 | 1/2009 | Goetz et al. |
| 2009/0082844 A1 | 3/2009 | Zacharias et al. |
| 2009/0082847 A1 | 3/2009 | Zacharias et al. |
| 2009/0088832 A1 | 4/2009 | Chew et al. |
| 2009/0125096 A1 | 5/2009 | Chu et al. |
| 2009/0138079 A1 | 5/2009 | Tuval et al. |
| 2009/0149946 A1 | 6/2009 | Dixon |
| 2009/0171438 A1 | 7/2009 | Chuter et al. |
| 2009/0171456 A1 | 7/2009 | Kveen et al. |
| 2009/0182407 A1 | 7/2009 | Leanna et al. |
| 2009/0182413 A1 | 7/2009 | Burkart et al. |
| 2009/0188964 A1 | 7/2009 | Orlov |
| 2009/0216314 A1 | 8/2009 | Quadri |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287290 A1 | 11/2009 | Macaulay et al. |
| 2009/0287296 A1 | 11/2009 | Manasse |
| 2010/0004740 A1 | 1/2010 | Seguin et al. |
| 2010/0114299 A1 | 5/2010 | Ben Muvhar et al. |
| 2010/0114305 A1 | 5/2010 | Kang et al. |
| 2010/0121076 A1 | 5/2010 | Taillefer et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2012/0022639 A1 | 1/2012 | Hacohen et al. |
| 2012/0041550 A1 | 2/2012 | Salahieh et al. |
| 2012/0078360 A1 | 3/2012 | Rafiee |
| 2012/0101572 A1 | 4/2012 | Kovalsky et al. |
| 2012/0123529 A1 | 5/2012 | Levi et al. |
| 2012/0271398 A1 | 10/2012 | Essinger et al. |
| 2012/0290062 A1 | 11/2012 | McNamara et al. |
| 2013/0006294 A1 | 1/2013 | Kashkarov et al. |
| 2013/0144375 A1 | 6/2013 | Giasolli et al. |
| 2013/0253635 A1 | 9/2013 | Straubinger et al. |
| 2013/0345786 A1 | 12/2013 | Behan |
| 2014/0163668 A1 | 6/2014 | Rafiee |
| 2014/0222139 A1 | 8/2014 | Nguyen et al. |
| 2014/0296973 A1 | 10/2014 | Bergheim et al. |
| 2014/0309728 A1 | 10/2014 | Dehdashtian et al. |
| 2014/0324160 A1 | 10/2014 | Benichou et al. |
| 2014/0336754 A1 | 11/2014 | Gurskis et al. |
| 2014/0350666 A1 | 11/2014 | Righini |
| 2014/0364943 A1 | 12/2014 | Conklin |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379077 A1 | 12/2014 | Tuval et al. |
| 2015/0012085 A1 | 1/2015 | Salahieh et al. |
| 2015/0018938 A1 | 1/2015 | Von Segesser et al. |
| 2015/0148731 A1 | 5/2015 | McNamara et al. |
| 2015/0297346 A1 | 10/2015 | Duffy et al. |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0279386 A1 | 9/2016 | Dale et al. |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |

FOREIGN PATENT DOCUMENTS

| | | |
|---|---|---|
| EP | 1171059 A1 | 1/2002 |
| EP | 1255510 A1 | 11/2002 |
| EP | 1259194 A1 | 11/2002 |
| EP | 1281375 A2 | 2/2003 |
| EP | 1369098 A1 | 12/2003 |
| EP | 1472996 A1 | 11/2004 |
| EP | 1734903 A1 | 12/2006 |
| EP | 1827558 A2 | 9/2007 |
| EP | 1239901 B1 | 10/2007 |
| EP | 2124826 A1 | 12/2009 |
| EP | 1935377 B1 | 3/2010 |
| EP | 2238947 A2 | 10/2010 |
| EP | 2308425 A1 | 4/2011 |
| EP | 2319458 A1 | 5/2011 |
| EP | 2398543 A1 | 12/2011 |
| EP | 2496182 A1 | 9/2012 |
| EP | 2750630 A1 | 7/2014 |

(56) References Cited

FOREIGN PATENT DOCUMENTS

| | | |
|---|---|---|
| EP | 2815723 A1 | 12/2014 |
| EP | 2815725 A1 | 12/2014 |
| EP | 2967858 A2 | 1/2016 |
| EP | 2168536 B1 | 4/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 1315844 A | 5/1973 |
| GB | 2245495 A | 1/1992 |
| GB | 2398245 A | 8/2004 |
| JP | 2002540889 A | 12/2002 |
| WO | 1997049355 A1 | 12/1997 |
| WO | 0053104 A1 | 9/2000 |
| WO | 0061034 A1 | 10/2000 |
| WO | 0135861 A1 | 5/2001 |
| WO | 0172239 A2 | 10/2001 |
| WO | 03092554 A1 | 11/2003 |
| WO | 2004030569 A2 | 4/2004 |
| WO | 2005011534 A1 | 2/2005 |
| WO | 2005041810 A2 | 5/2005 |
| WO | 2006085304 A2 | 8/2006 |
| WO | 2006089236 A1 | 8/2006 |
| WO | 2007025028 A1 | 3/2007 |
| WO | 2007034488 A2 | 3/2007 |
| WO | 2007058857 A2 | 5/2007 |
| WO | 2007123658 A1 | 11/2007 |
| WO | 2007134290 A2 | 11/2007 |
| WO | 2008005535 A2 | 1/2008 |
| WO | 2008013915 A2 | 1/2008 |
| WO | 2008070797 A2 | 6/2008 |
| WO | 2008125153 A1 | 10/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2010004009 A2 | 1/2010 |
| WO | 2010005524 A2 | 1/2010 |
| WO | 2010008549 A1 | 1/2010 |
| WO | 2010022138 A2 | 2/2010 |
| WO | 2010037141 A1 | 4/2010 |
| WO | 2010040009 A1 | 4/2010 |
| WO | 2010057262 A1 | 5/2010 |
| WO | 2010121076 A2 | 10/2010 |
| WO | 2011025945 A1 | 3/2011 |
| WO | 2011057087 A1 | 5/2011 |
| WO | 2011111047 A2 | 9/2011 |
| WO | 2012035279 A1 | 3/2012 |

OTHER PUBLICATIONS

Bavaria, Joseph E. M.D.: "CardiAQ Valve Technologies: Transcatheter Mitral Valve Implantation," Sep. 21, 2009.
Berreklouw, Eric, MD, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7pages, Applicant believes this may have been available online as early as Feb. 4, 2011.
Boudjemline, Younes, et al., "Steps Toward the Percutaneous Replacement of Atrioventricular Valves," JACC, vol. 46, No. 2, Jul. 19, 2005:360-5.
CardiAQ Valve Technologies, "Innovations in Heart Valve Therapy," In3 San Francisco, Jun. 18, 2008, PowerPoint presentation in 19 slides.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31, Applicant believes this may have been available as early as Dec. 2006.
Feldman, Ted, MD. "Prospects for Percutaneous Valve Therapies," Circulation 2007;116:2866-2877. Applicant believes that this may be available as early as Dec. 11, 2007.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Horvath et al.: "Transapical Aortic Valve Replacement under Real-time Magnetic Resonance Imaging Guidance: Experimental Results with Balloon—Expandable and Self-Expanding Stents," http://www.ncbi.nlm.nih.gov/pmc/articles/PMC3038190/. Jun. 2011.
Karimi, Houshang, et al., "Percutaneous Valve Therapies," SIS 2007 Yearbook, Chapter 11, pp. 1-11.
Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. of 2005.
Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.
Mack, Michael, M.D., "Antegrade Transcatheter Mitral valve Implantation: A Short-term Experience in Swine Model," Applicant believes this may have been presented on May 2011 at TVT.
Mack, Michael, M.D., "Antegrade Transcatheter Mitral valve Implantation: On-Going Experience in Swine Model," Applicant believes this may have been presented on Nov. 2011 at TCT.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Neovasc corporate presentation, Oct. 2009, available at http://www.neovasc.com/investors/documents/Neovasc-Corporate-Presentation--October-2009.pdf.
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. 2008.

(56) References Cited

OTHER PUBLICATIONS

Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.

Quadri, Arshad M.D., "Transcatheter Mitral Valve Implantation (TMVI) (An Acute In Vivo Study)," Applicant believes his may have been presented on Sep. 22, 2010 at TCT.

Raiz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.

Ratz, J. Brent, "In3 Company Overview," Jun. 24, 2009.

Ratz, J. Brent, "LSI EMT Spotlight," May 15, 2009.

Ruiz, Carlos E., "Overview of Novel Transcatheter Valve Technologies," Applicant believes this may have been presented on May 27, 2010 at EuroPCR.

Seidel, Wolfgang, et al., "A Mitral Valve Prosthesis and a Study of Thrombosis on Heart Valves in Dogs," JSR—vol. II, No. 3—May, 1962, submitted for publication Oct. 9, 1961.

Spillner, J. et al., "New Sutureless 'Atrial- Mitral-Valve Prosthesis' for Minimally Invasive Mitral Valve Therapy," Textile Research Journal, 2010, in 7 pages, Applicant believes this may have been available as early as Aug. 9, 2010.

Van Mieghem, et al., "Anatomy of the Mitral Valvular Complez and Its Implications for Transcatheter Interventions for Mitral Regurgitation," J. Am. Coll. Cardiol., 56:617-626 (Aug. 17, 2010).

"Company Overview," at TVT on Jun. 25, 2009.

"Update," Applicant believes this may have been presented on Jun. 6, 2010 at TVT.

* cited by examiner

*FIG. 5C*
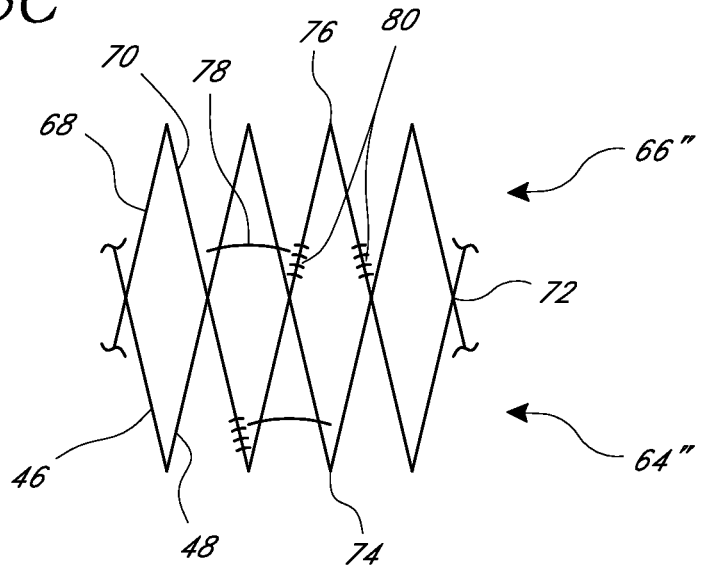
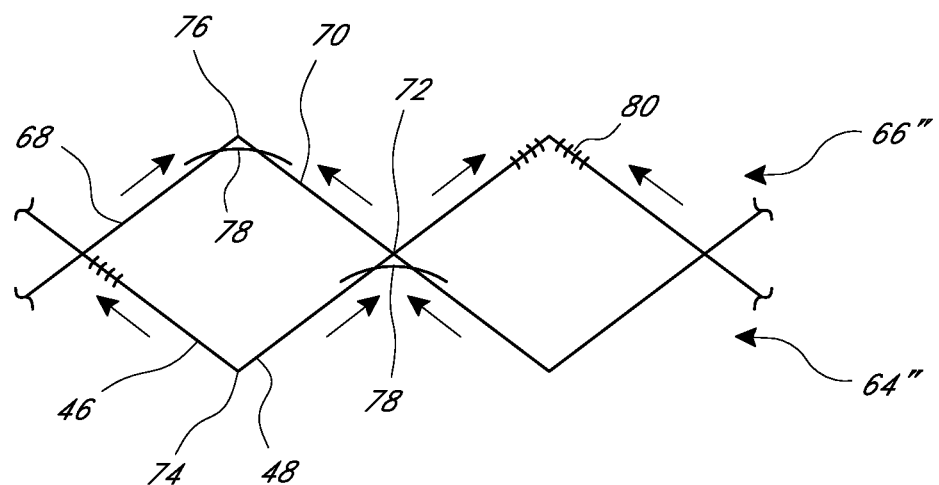
*FIG. 5D*

REPLACEMENT HEART VALVES, DELIVERY DEVICES AND METHODS

CROSS-REFERENCE TO RELATED APPLICATIONS

This application is a continuation of U.S. application Ser. No. 14/702,233, filed May 1, 2015, now U.S. Pat. No. 9,949,827, which is a continuation of U.S. application Ser. No. 13/756,424, filed Jan. 31, 2013, now U.S. Pat. No. 9,023,100, which is a continuation of U.S. application Ser. No. 13/244,080, filed Sep. 23, 2011, now U.S. Pat. No. 8,652,203, which claims priority to U.S. Provisional Appl. No. 61/385,651, filed Sep. 23, 2010. This application is also related to U.S. application Ser. No. 12/569,856, filed Sep. 29, 2009, Ser. No. 12/761,349, filed Apr. 15, 2010, and Ser. No. 13/165,721, filed Jun. 21, 2011. The entirety of each of the above applications is incorporated by reference herein and is to be considered a part of this specification.

BACKGROUND

Field of the Invention

Certain embodiments disclosed herein relate generally to replacement valves for a vascular system, delivery devices for the replacement valves, and related delivery methods, among other things. In particular, the valves relate to replacement heart valves, such as for the mitral valve.

Description of the Related Art

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatus to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves, that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of replacement heart valves that can be compacted for delivery and then controllably expanded for controlled placement, and the related delivery devices have proven to be particularly challenging.

SUMMARY OF THE INVENTION

Accordingly, there is in the need of the art for improved replacement heart valves, delivery devices, and delivery methods, among other things.

In some embodiments a replacement heart valve can comprise an expandable frame, and a valve body. The expandable frame can be configured to engage a native valve annulus, wherein the frame extends longitudinally between an upstream end and a downstream end, the frame having a foreshortening portion at or adjacent the downstream end, the foreshortening portion comprising foreshortening cells that are longitudinally expanded when the frame is in a radially compacted state and longitudinally contracted when the frame is in a radially expanded state. The valve body can be coupled to the frame, the valve body coupled to the frame in the foreshortening portion in a manner so that the frame foreshortening portion can move longitudinally relative to the valve body. Upon radial compaction of the implant, the frame foreshortening portion can longitudinally expand but moves relative to the valve body so that the valve body substantially retains its longitudinal length.

According to some embodiments, the valve body can have a downstream end that is generally aligned with a downstream end of the frame foreshortening portion, but is not connected to the downstream end of the frame foreshortening portion. A first longitudinal distance can exist between the downstream end of the frame foreshortening portion downstream end and the downstream end of the valve body when the frame is in a radially expanded configuration, and a second longitudinal distance exists between the downstream end of the frame foreshortening portion downstream end and the downstream end of the valve body when the frame is in a radially compacted configuration, the second longitudinal distance being greater than the first longitudinal distance.

In some embodiments, the valve body can be slidably coupled to a downstream portion of the frame and substantially non-slidably coupled to an upstream portion of the frame. The expandable frame may further comprise a non-foreshortening portion at or adjacent the upstream end, the non-foreshortening portion comprising longitudinal struts. The non-foreshortening portion can be configured to substantially maintain its longitudinal length as between the radially compacted state and the radially expanded state. The longitudinal struts can extend upstream from the foreshortening cells. The valve body can be slidably coupled to a downstream portion of the frame and substantially non-slidably coupled to an upstream portion of the frame. The valve may also further comprise a substantially inelastic band at the upstream end of the expandable frame.

In some embodiments, replacement heart valve can comprise an expandable frame configured to engage a native valve annulus, wherein the frame extends longitudinally between an upstream end and a downstream end, the frame having a foreshortening portion at or adjacent the downstream end, the foreshortening portion comprising foreshortening cells that are longitudinally expanded when the frame is in a radially compacted state and longitudinally contracted when the frame is in a radially expanded state, a valve body coupled to the frame, and a support band positioned within the frame at the upstream end.

A delivery device for delivering a replacement heart valve according to some embodiments can comprise an inner support for receiving a replacement heart valve, an inner retainer ring on the inner support, and an outer retainer ring to slidably engage the inner retainer ring to secure a proximal end of the replacement heart valve on the delivery device.

Some embodiments of delivery device can further include a floating sheath to slidably cover a central region of the replacement heart valve between the proximal end and a distal end while the replacement heart valve is in a radially compacted state and/or an outer sheath to slidably cover the replacement heart valve in the radially compacted state, as well as the outer retainer ring, the inner retainer ring, and floating sheath, wherein the floating sheath is connected to the outer sheath with one or more tension members such that withdrawal of the outer sheath from covering the replacement heart valve can also cause the floating sheath to withdraw from covering the replacement heart valve. The outer sheath may have a first withdrawal position where at least the distal end of the replacement heart valve is uncovered and the floating sheath remains covering the central region. The outer sheath may have a second withdrawal position where the floating sheath does not cover the central region.

A method of treating valve insufficiency of a mitral valve of a patient by delivering a replacement valve can comprise one or more of the following steps. Providing a replacement valve mounted on a delivery device, the replacement valve comprising a radially expandable frame having an upstream end and a downstream end, the frame further comprising a plurality of first anchors directed toward the upstream end. Delivering the replacement valve to a native mitral valve annulus while the replacement valve is in a radially compacted state, the native mitral valve annulus having two or more native valve leaflets. Positioning the replacement valve so that tips of the plurality of first anchors are downstream of the native valve leaflets. Exposing a portion of the downstream end of the replacement valve so that the plurality of first anchors extend radially from the delivery device and the anchor tips are positioned to an outer side of the native leaflets. Moving the replacement valve in an upstream direction so that tips of the plurality of first anchors engage a downstream side of the native mitral valve annulus. After the plurality of first anchors engage the native mitral valve annulus, releasing the replacement valve from the delivery device and allowing the frame to expand to a radially expanded state.

In some embodiments, a method may also include one or more of the following steps. Wherein the downstream end of the frame has a foreshortening portion configured to longitudinally expand when in the radially compacted state and longitudinally contract when the foreshortening portion is in the radially expanded state and the upstream end maintains a substantially constant longitudinal length in the expanded state and in the compacted state. Wherein a downstream portion of the frame foreshortens and flares radially outward as the frame expands to the expanded state. Wherein moving the replacement valve in an upstream direction comprises engaging and compacting or folding the native valve leaflets with the plurality of first anchors. Wherein moving the replacement valve in an upstream direction so that tips of the plurality of first anchors engage a downstream side of the native valve annulus comprises engaging a posterior leaflet. After engaging the posterior leaflet repositioning the replacement valve, and engaging an anterior leaflet with the plurality of first anchors. Engaging an upstream side of the native mitral valve annulus with a plurality of second anchors. Exposing a portion of the downstream end of the replacement valve so that the plurality of first anchors extend radially from the delivery device further comprises expanding the frame to a first expanded state. Expanding the frame to a second expanded state and moving the replacement valve in an upstream direction so that tips of the plurality of first anchors engage another part of the downstream side of the native mitral valve annulus. Wherein releasing the replacement valve from the delivery device and allowing the frame to expand to a radially expanded state comprising expanding the frame to a third expanded state.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

FIG. 5C is a side view of a portion of the cells of the compacted-state replacement heart valve of FIG. 5B.

FIG. 5D is a side view of a portion of the cells of the expanded-state replacement heart valve of FIG. 5A.

DETAILED DESCRIPTION OF PREFERRED EMBODIMENTS

The present specification and drawings provide aspects and features of the disclosure in the context of several embodiments of replacement heart valves, delivery devices and methods that are configured for use in the vasculature of a patient, such as for replacement of natural heart valves in a patient. These embodiments may be discussed in connection with replacing specific valves such as the patient's aortic or mitral valve. However, it is to be understood that the features and concepts discussed herein can be applied to products other than heart valve implants. For example, the controlled positioning, deployment, and securing features described herein can be applied to medical implants for use elsewhere in the body, such as within a vein, or the like. In addition, particular features of a valve, delivery device, etc. should not be taken as limiting, and features of any one embodiment discussed herein can be combined with features of other embodiments as desired and when appropriate.

Figure 1:
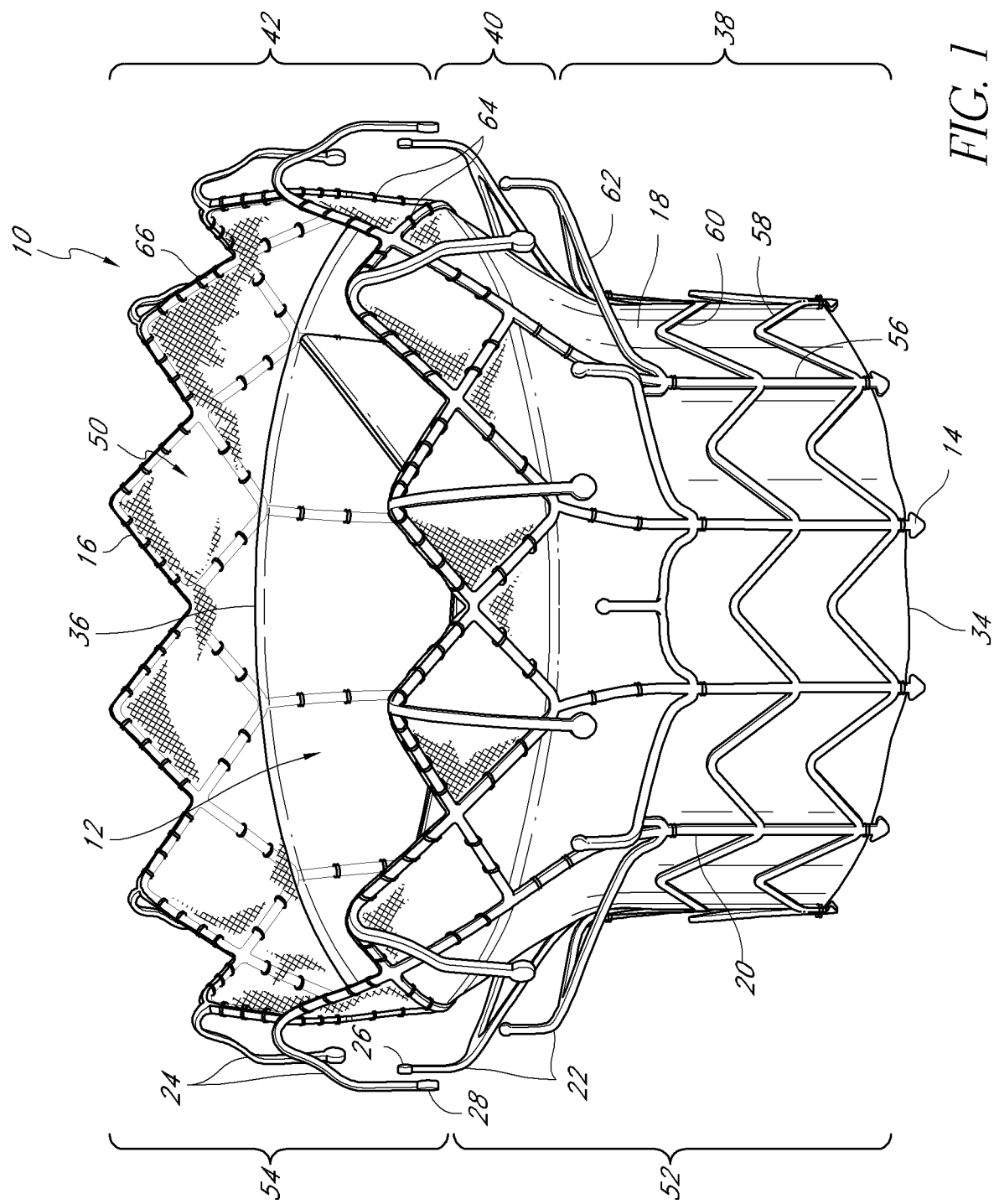
FIG. 1 is a perspective view of one embodiment of a replacement heart valve.
Figure 2:
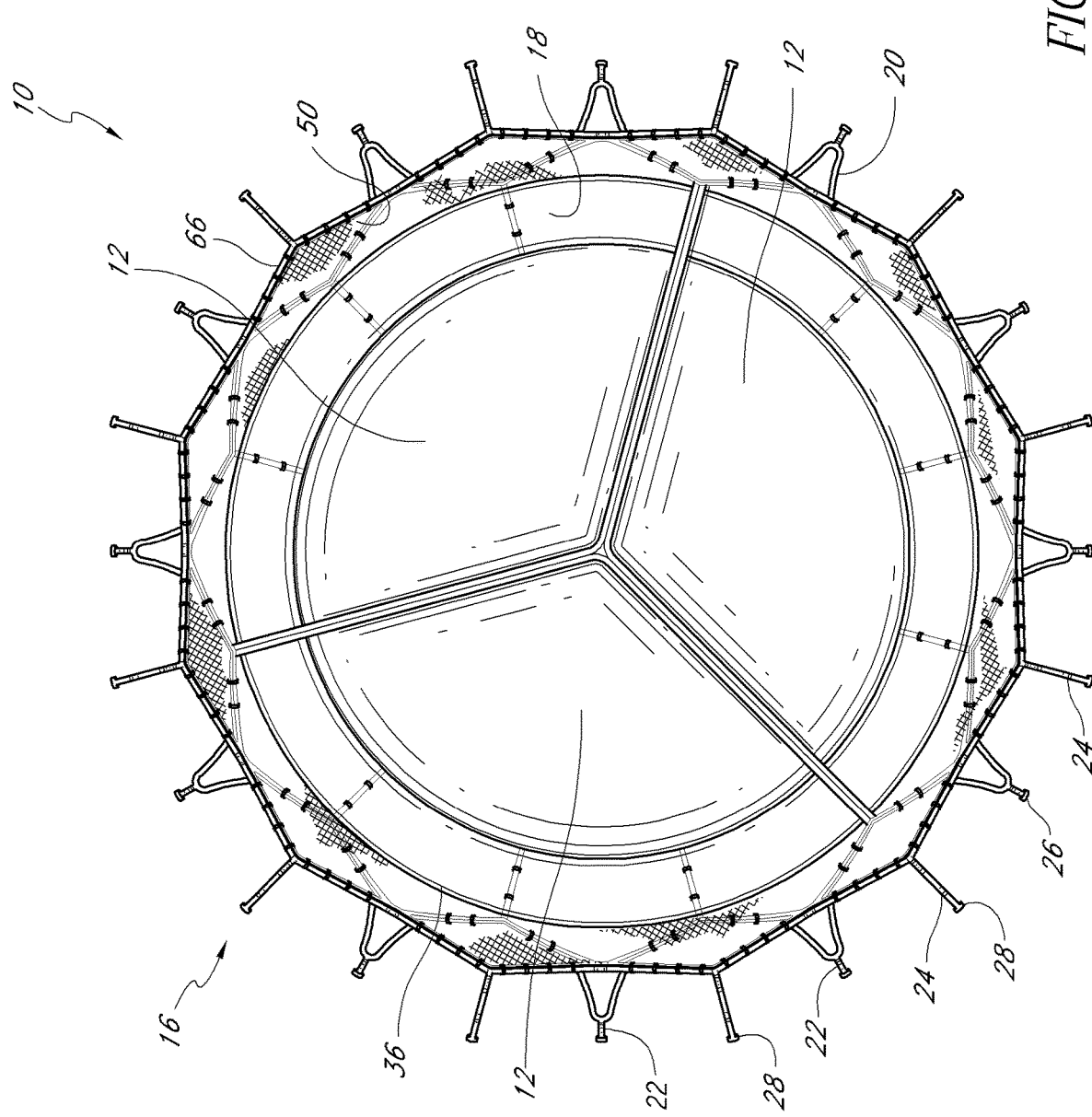
FIG. 2 is a view looking upstream through the replacement heart valve of FIG. 1.

With initial reference to FIGS. 1 and 2, an embodiment of a replacement heart valve 10 is shown. The illustrated replacement heart valve 10 is designed to replace a damaged or diseased native heart valve such as a mitral valve. The replacement heart valve 10 includes a self-expanding frame 20 to which a plurality of valve leaflets 12 are attached.

The plurality of valve leaflets 12 can function in a manner similar to the natural mitral valve, or to other valves in the vascular system. The plurality of valve leaflets 12 can open in a first position and then engage one another to close the valve in a second position. The plurality of valve leaflets 12 can be made to function as a one way valve such that flow in one direction opens the valve and flow in a second direction opposite the first direction closes the valve. The replacement heart valve 10 can be constructed so as to open naturally with the beating of the heart. For example, the plurality of valve leaflets 12 can be open during diastole and closed during systole. The valve can include many different components as will be discussed in detail below.

To aid in the description of the replacement heart valve 10, certain directional or relative terms may be used herein. The illustrated replacement heart valve 10 is a one-way valve, thus the term "upstream" refers to the end or section closest to the inflow of blood or other fluid into the valve and "downstream" refers to the end or section closest to the outflow of blood or other fluid from the valve. As will be described, the replacement heart valve 10 is generally implanted by moving the replacement heart valve 10 within a vessel towards the diseased or damaged native valve with the flow of fluid. Thus, the term "proximal" coincides with upstream and "distal" coincides with downstream. It should be understood that the valve can also be implanted by moving the replacement heart valve in the opposite direction. The term "longitudinal" refers to a direction, length or a location between the proximal end 14 and the distal end 16 of the replacement heart valve 10. The term "lateral" refers to a direction, length or location perpendicular to the longitudinal direction, length or location.

Still referring to FIG. 1, the shape of the illustrated replacement heart valve 10 can be generally referred to as having an upstream portion 38, a transition portion 40 and a downstream portion 42. The replacement heart valve 10 can be generally cylindrical in the longitudinal direction with the same or a varying diameter or outer perimeter. In the illustrated embodiment, the upstream portion 38 has an inflow diameter at the proximal end 14 and the downstream portion 42 preferably has an outflow diameter at the distal end 16. The upstream portion 38 and downstream portion 42 are generally cylindrical based on either the inflow diameter or the outflow diameter. As the outflow diameter is greater than the inflow diameter, a generally conical transition portion 40 is positioned between the proximal 14 and distal 16 ends. It will be understood that, in some embodiments, the replacement heart valve 10 may not have a transition portion 40, or that the transition portion 40 may be very abrupt and short. In addition, in some embodiments the transition portion 40 may be coextensive with either or both of the upstream portion 38 and the downstream portion 42. Some embodiments have a larger inflow dimension than the outflow dimension. In addition, in some embodiments the geometry of the replacement heart valve 10 can include one or more portions that are conical, spherical, parabolic, oval, convex, concave, or the like, or any combination thereof.

Finally, a non-foreshortening portion 52 and a foreshortening portion 54 are also referenced with the illustrated replacement heart valve 10. As will be described in more detail below, foreshortening refers to the idea that as the replacement heart valve 10 changes from the compacted or collapsed position to the expanded position the longitudinal length of the replacement heart valve 10 decreases in the foreshortening portion 54 but not in the non-foreshortening portion 52.

Replacement Heart Valve Frame

As has been mentioned, the replacement heart valve 10 includes a self-expanding frame 20 to which a plurality of valve leaflets 12 are attached. Other components of the valve may also be attached to the frame 20. It is to be understood that some embodiments may not employ a self expanding frame but may, for example, employ a balloon or the like to expand and deploy the frame.

The frame 20 can serve one or more different and unique purposes. For example, the frame 20 can serve as structural support for the valve, an anchoring mechanism to attach the valve to the vasculature, an attachment device to attach valve components to, a device to facilitate delivery of the valve and a device to maintain position of the valve after delivery.

The frame 20 can be made of many different materials, but is preferably made from metal. For example, the frame 20 can be a wireframe or a metal tube that has been cut or etched to remove all but a metal skeleton. The frame 20 can be constructed from a metal tube, such as a nitinol tube. In some embodiments, the frame 20 can be made from a shape memory material. The frame 20 can further be expanded and/or compressed and/or otherwise worked to have the desired introduction and implantation configurations.

As can be seen with particular reference to FIG. 1, the frame 20 includes a number of struts or members that collectively make up the frame 20. These struts can include longitudinal struts 56 and undulating struts, such as undulating struts forming one or more rings 58, 60, 62, 64, and 66. It will be understood that the frame 20 can include any number of longitudinal struts, undulating struts, and rings. The upstream 38, transition 40 and downstream 42 portions may all include more or less longitudinal struts, undulating struts, and rings than those shown herein, as well as, other configurations of the same.

Figure 3:
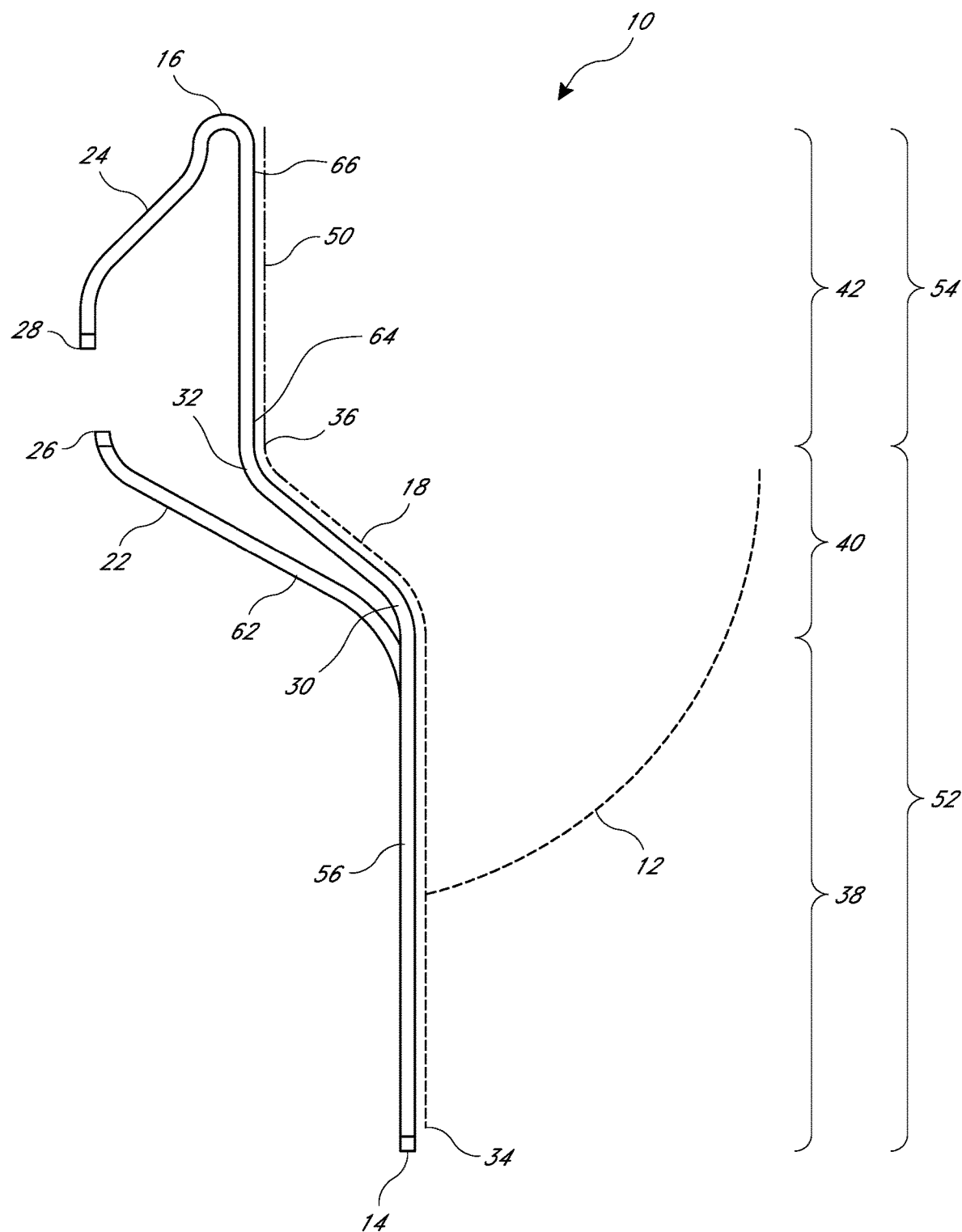
FIG. 3 is a schematic detail side view of the replacement heart valve of FIG. 1.

As mentioned previously, the replacement heart valve 10 has a non-foreshortening portion 52 and a foreshortening portion 54. These portions can be defined by the frame 20 and the positioning of various types of struts along the frame 20. Referring now to FIGS. 1 and 3, it can be seen that the longitudinal struts 56 span the length of the non-foreshortening portion 52. Distal or downstream portions of the longitudinal struts 56 make up the transition portion 40, in which the struts 56 bend at bending stage 30 so as to flare radially outwardly and then bend again at bending stage 32 so as to stop expanding in radius and attach to the foreshortening portion 54 of the frame 20. As such, the frame 20 is generally divided into the upstream portion 38 made up of the first diameter, the transition portion 40 at which the diameter is expanding, and the downstream portion 42 with the larger second diameter. The downstream portion 42 also includes the foreshortening portion 54.

First 58, second 60, and third 62 rings made up of undulating struts are connected to the longitudinal struts 56 in the non-foreshortening portion 52. The illustrated first 58 and second 60 rings are of generally the same size, however, the struts in the third ring 62 are substantially larger and longer than the struts in the first 58 and second 60 rings. For example, the struts of the first 58 and second 60 rings can be about half as long as the struts of the third ring 62, or shorter. Additionally, upstream anchors 22 extend from the free apices of the struts in the third ring 62. As best shown in FIG. 3, the struts in the third ring 62 preferably are flared radially out at a more dramatic angle than is the longitudinal strut 56 at the transition portion 40. In the illustrated embodiment, the third ring struts 62 can be considered part of the upstream anchors 22.

Referring to FIGS. 1 and 3, a fourth ring 64 is attached to the distal end of the longitudinal struts 56 at an apex of the fourth ring 64. A fifth ring 66 attaches to the fourth ring 66 on the side opposite the longitudinal struts 56. The fifth ring 66 can be a mirror image of the fourth ring 64. In some embodiments, additional rings of undulating struts can be included in any part of the frame. For example, sixth and/or seventh rings can be positioned downstream of the fifth ring.

The fourth 64 and fifth 66 rings are made up of undulating struts and can make up the foreshortening portion 54. Expansion of the replacement heart valve 10 causes the struts of the fourth ring 64 to move farther apart such that they are at a greater angle relative to one another. Thus, they move from a relatively vertical orientation to a more horizontal orientation. This also causes the ring to shrink in vertical height. The fifth ring exhibits similar behavior when the valve 10 expands. This movement of the fourth 64 and fifth 66 rings results in foreshortening of the frame 20.

Opposing anchors 22, 24 can be constructed on the frame 20 so that preferably their tips 26, 28 move closer together as the frame foreshortens. This can allow the anchors 22, 24 to grasp opposite sides of the native mitral annulus or any other tissue that is perpendicular to the axis of the frame.

The anchors 22, 24 and anchor tips 26, 28 can be located anywhere along the frame 20 just so long as at least one of the anchors is connected to the foreshortening portion 54 to thereby move with the foreshortening portion 54. As shown, both of the anchor tips 26, 28 are located in the foreshortening portion 54. The foreshortening portion can also be positioned anywhere along the frame.

Preferably, each of the anchors 22, 24 also extends generally radially outwardly from the frame 20 so that the anchor tips 26, 28 are generally spaced away from the rest of the frame 20. In some embodiments, all or part of the structure connected to the anchor tip and extending radially from the frame, including one or more rings and/or struts, can be considered part of the anchor. The anchors can include a base located on the anchor on a side opposite the tip. The base can be for example where the anchor begins to extend from or away from the frame 20.

In some embodiments, each of the anchors can extend radially outwardly from the frame at an anchor base and terminate at an anchor tip. The anchors can be connected to the frame at one of many different locations including apices, junctions, other parts of struts, etc. The anchors can comprise first, second, third, or more spaced apart bending stages along the length of each anchor. The anchors can also extend either upstream or downstream before and/or after one or more of the bending stages. A portion of the anchor may extend with the frame before any bending stages. An example anchor can include first and second bending stages with a portion between the second bending stage and the anchor tip being generally parallel to an axis of the frame. Another example, can include first, second and third spaced apart bending stages, and wherein in the first bending stage the anchor is bent radially inwardly, in the second bending stage the anchor is bent radially outwardly, and in the third bending stage the anchor is bent radially inwardly. In the second bending stage the anchor can be bent about 180 degrees.

In preferred embodiments, the replacement heart valve 10 may be deployed into a heart valve annulus, and positioned when compacted so that the anchor tips 26, 28 of the opposing anchors 22, 24 are disposed on opposite sides of the native annulus. As the replacement heart valve 10 is expanded, the opposing anchors are drawn closer together so as to grasp opposite sides of the native annulus with the anchor tips 26, 28 and securely hold the replacement heart valve 10 in position. As such, the replacement heart valve 10 can be held securely in position without requiring a substantial radial force against the native annulus. The foreshortening portion 54 can be used to move the anchor tips 26, 28 closer together as the replacement heart valve 10 moves to the expanded position to thereby engage the native valve annulus.

Notably, in this embodiment the native annulus which is intended to be gripped between the anchor tips 26, 28 will be engaged by the foreshortening portion 54 of the frame 20, and will not engage the transition portion 40 of the frame 20. Rather, in a mitral placement, the upstream 38 and transition 40 portions of the replacement valve 10 will not necessarily be disposed within the annulus but mostly or entirely in the atrium.

Applicant's U.S. patent application Ser. No. 12/084,586, which was published on Aug. 27, 2009 as U.S. Publication No. 2009/0216314, discusses embodiments of foreshortening stents with anchors, and can be referred to for further discussion of certain aspects of the illustrated embodiments. Applicant's U.S. patent application Ser. No. 13/165,721, filed on Jun. 21, 2011, discusses embodiments of foreshortening frames with anchors, and can be referred to for further discussion of certain aspects of the illustrated embodiments. The above applications are incorporated in their entirety by reference herein with particular reference to the discussion concerning structure and operation of embodiments of foreshortening structures, particularly foreshortening structures having anchors.

Replacement Heart Valve Body

The replacement heart valve can include a valve body that is made up of one or more components. In some embodiments, the valve body only includes a plurality of valve leaflets. In other embodiments, the valve body may also include one or more of an outer valve skirt, a connection skirt, and a support band.

As has been mentioned, a plurality of valve leaflets 12 are attached to the self-expanding frame 20 (FIGS. 2 and 3). The plurality of valve leaflets 12 can function in a manner similar to the natural mitral valve to open and close as appropriate and thereby control blood flow.

The leaflets 12 can be one of many different shapes and configurations. There can be two, three or more leaflets 12. The leaflets 12 can be cut from a flat, tissue material such as pericardium. Preferably, upstream portions of the leaflets are generally curved. The curvature and size of the pattern cuts, and particularly the curvature of the side edges, can be chosen so that the valve fits within the particular shape defined by the frame 20.

The leaflets 12 can also be positioned in any portion of the frame. The leaflets 12 can be positioned solely within any one of the upstream portion 38, the transition portion 40, and the downstream portion 42. The leaflets can also extend between different diameter sections of the frame 20. Looking to FIG. 3, it can be seen that in some embodiments, the leaflets 12 extend from the upstream portion 38 to the end of the transition portion 40. The 12 leaflets 12 can alternatively extend from any part of one of the upstream portion 38, the transition portion 40, and the downstream portion 42 to any part of one of the upstream portion 38, the transition portion 40, and the downstream portion 42.

In some embodiments, the leaflets 12 can be coupled to the outwardly flaring portion of the valve skirt 18 in the transition portion 40. In this position, the leaflets can be at least partially within the native mitral valve annulus upon deployment, closer to the left ventricle, and closer to a native leaflet position.

The replacement heart valve 10 can further include an outer valve skirt 18. The outer valve skirt 18 can be configured to direct fluid to the valve leaflets 12. The outer valve skirt 18 can also be used at partially to control how fluid flows through and/or around the replacement heart valve 10. The outer valve skirt 18 can surround at least a portion of the valve and be connected to the valve leaflets 12. In some embodiments, the outer valve skirt 18 can form an inner wall connected to and positioned within the frame 20.

The outer valve skirt 18 can extend the length of the frame 20 or it can extend along only part of the length of the frame 20. In some embodiments, the ends 14, 16 of the replacement heart valve 10 can coincide with the inflow 34 and outflow 36 ends of the outer valve skirt 18. In the illustrated embodiment of FIGS. 1-3, the inflow end 34 substantially coincides with one end 14 of the replacement heart valve 10 while the other end 16 of the replacement heart valve 10 extends past the outflow end 36 of the valve body.

The shape of the outer valve skirt 18 can substantially correspond to that of the frame 20, with for example, different diameter sections and a transition between them. Other shapes and configurations can also be used.

The valve leaflets 12 can extend along all or part of the length of the outer valve skirt 18, and including all or part of the reduced and increasing diameter portions, i.e., the upstream 38 and transition 40 portions, as shown. In some embodiments, the leaflets 12 can also span all or part of the length of the downstream portion 42, together with or separate from the outer valve skirt 18.

In the illustrated embodiments, the outer valve skirt 18 is attached to the frame 20 and the leaflets 12 are attached to the outer valve skirt 18. Preferably, the outer valve skirt 18 is also formed of a pericardium tissue similar to the leaflets 12.

The outer valve skirt 18 can be constructed in multiple different ways. For example, the outer valve skirt 18 can be made by cutting out one or more pieces from flat tissue material and sewing the tissue together to form the outer valve skirt with a flared transition portion. Preferably, the outer valve skirt 18 is constructed of a tissue that is flexible, but not particularly expansive and stretchy.

As best shown in FIGS. 1-3, the replacement heart valve 10 can also include a connection skirt 50. The connection skirt 50 can be attached to one or both of the frame 20 and the outer valve skirt 18. The connection skirt 50 can function and/or provide benefits similar to the outer valve skirt 18. For example, the connection skirt 50 can be used to direct fluid flow into, out of, and/or around the replacement heart valve 10. The connection skirt 50 can also be made to move with the foreshortening portion 54 of the frame 20.

The connection skirt 50 can be made of knit polyester or another stretchable or flexible fabric. In some embodiments, the connection skirt 50 is made from a material that is more flexible than the outer valve skirt material and/or the valve leaflet material.

As shown, the connection skirt 50 is sewn to the outflow end 36 of the outer valve skirt 18 and is also attached to the frame 20 in the foreshortening portion. The upstream edge of the connection skirt 50 is generally straight so as to correspond to the downstream edge or outflow end 36 of the outer valve skirt 18 and contribute to an advantageous seam structure. The downstream end of the connection skirt 50 can be straight, curved, or have any other desired configuration. For example, the connection skirt 50 is shown with undulations patterned to generally correspond to the undulations at the end 16 of the frame 20. It is to be understood that other configurations of the connection skirt 50 can also be employed.

Figure 4:
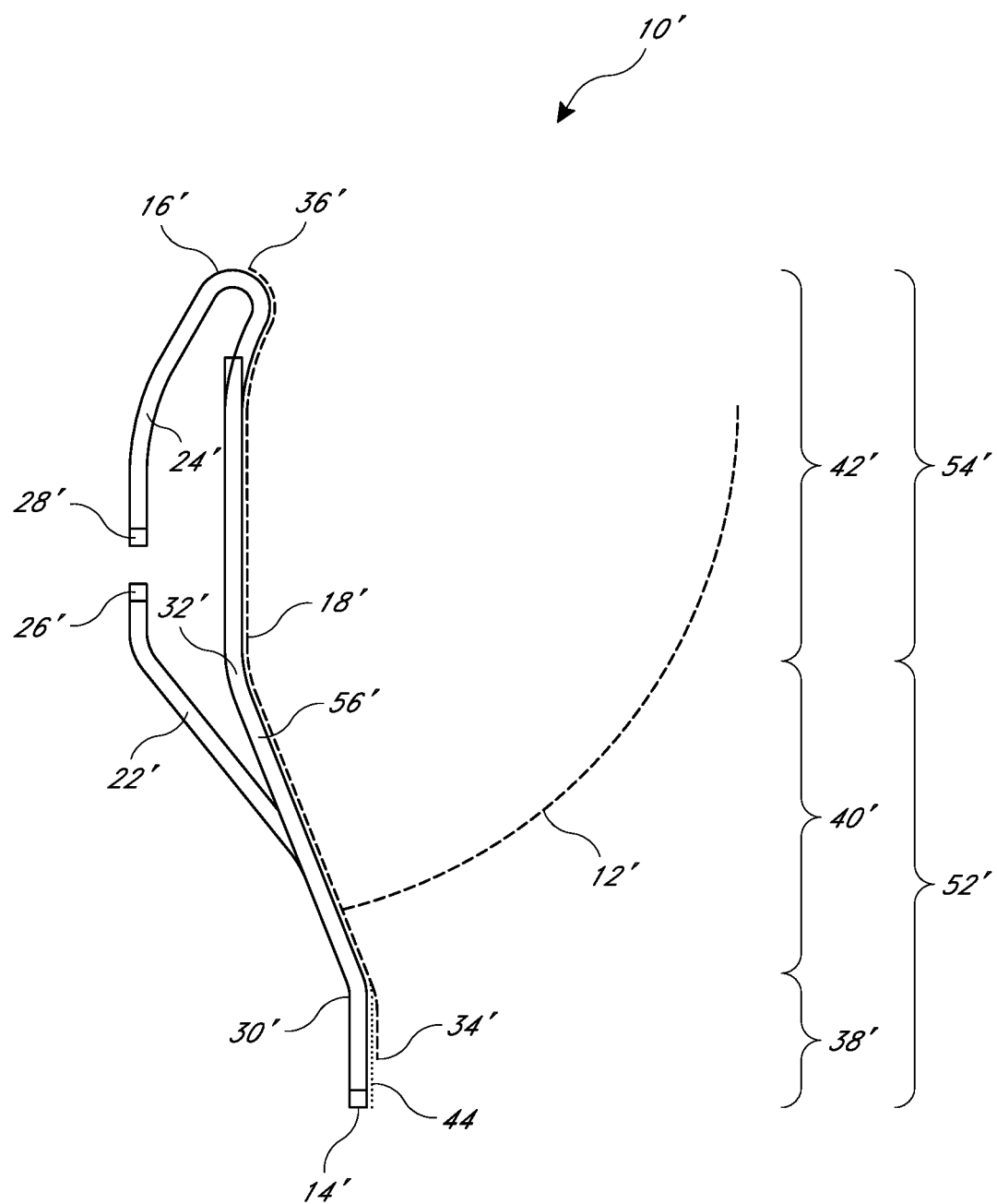
FIG. 4 shows a schematic detail side view of another embodiment of a replacement heart valve.

The replacement heart valve 10 can also include a support band 44. FIG. 4 illustrates a detail view of another embodiment of a replacement heart valve 10' including a support band 44. Numerical reference to components is the same as previously described, except that a prime symbol (') has been added to the reference. Where such references occur, it is to be understood that the components are the same or substantially similar to previously-described components.

The support band 44 may be placed or positioned around or within the frame 20' at the proximal end. The support band 44 can be used to reinforce and/or constrain the frame 20'. The support band 44 can help to control the expansion of the frame 20' from the compacted to the expanded state. The support band 44 can also be used to reduce the amount of motion that occurs at the upstream portion 38' and/or at the proximal end 14' after the replacement heart valve 10' has been implanted within the mitral heart valve or other location.

In some embodiments, the support band 44 may comprise a polyester fabric band. The support band 44 may comprise a no-stretch or limited stretch material. Preferably the support band 44 is not made of an elastic material or a material known to have high elasticity. In some embodiments, the support band 44 is made from a material that is less flexible than the outer valve skirt material and/or the valve leaflet material. The distal and proximal ends of the support band 44 can be straight, curved, undulating with the undulations of frame, or any other desired configuration.

The support band 44 can be connected to the valve frame with a plurality of stitches, loops, knots, staples, or other types of connections. In some embodiments, the frame 20' can be sandwiched between two sides or layers of the support band 44. Preferably, the support band 44 is a single layer positioned within and attached to the frame 20' with a plurality of stitches around one or more of the longitudinal and/or undulating struts.

Viewing FIG. 4 in comparison to FIG. 3, it can be seen that the leaflets 12', 12 are positioned lower in the valve, or closer to the proximal end 14', 14 in FIG. 4. The support band 44 can reduce the movement and the moment at the proximal end 14' allowing the valve to function more smoothly.

Still referring to FIG. 4, it can also be seen that this embodiment does not include a connection skirt so that the distal end 36' of the outer valve skirt 18' extends to the distal end 16' of the valve.

The replacement heart valve 10' may include a first ring of undulating struts in the upstream portion 38', and a second ring of undulating struts in the transition portion 40', including part of the anchor 22'. Third, fourth, and fifth rings are preferably located in the downstream portion 42' forming two rows of adjacent diamond- or oval-shaped cells. In some embodiments, the downstream anchors 24' extend from the junction of the fourth and fifth rings.

Additional example replacement heart valves with valve bodies are discussed in detail in U.S. application Ser. No. 12/569,856, filed Sep. 29, 2009 and Ser. No. 13/165,721, filed Jun. 21, 2011, both of which are incorporated by reference herein in their entirety and are to be considered a part of this specification.

Expansion and Compaction of Replacement Heart Valve

FIGS. 5A-D illustrate another embodiment of a replacement heart valve 10". The illustrated replacement heart valve 10" is designed to replace a diseased native mitral valve. The replacement heart valve includes a self-expanding frame 20" to which a valve body is attached. The valve body includes an outer valve skirt 18" and flexible leaflets that open and close, as discussed above. The replacement heart valve 10" also includes a plurality of fasteners, which connect the valve body to the frame 20, as will be described in more detail below.

Figure 5A:
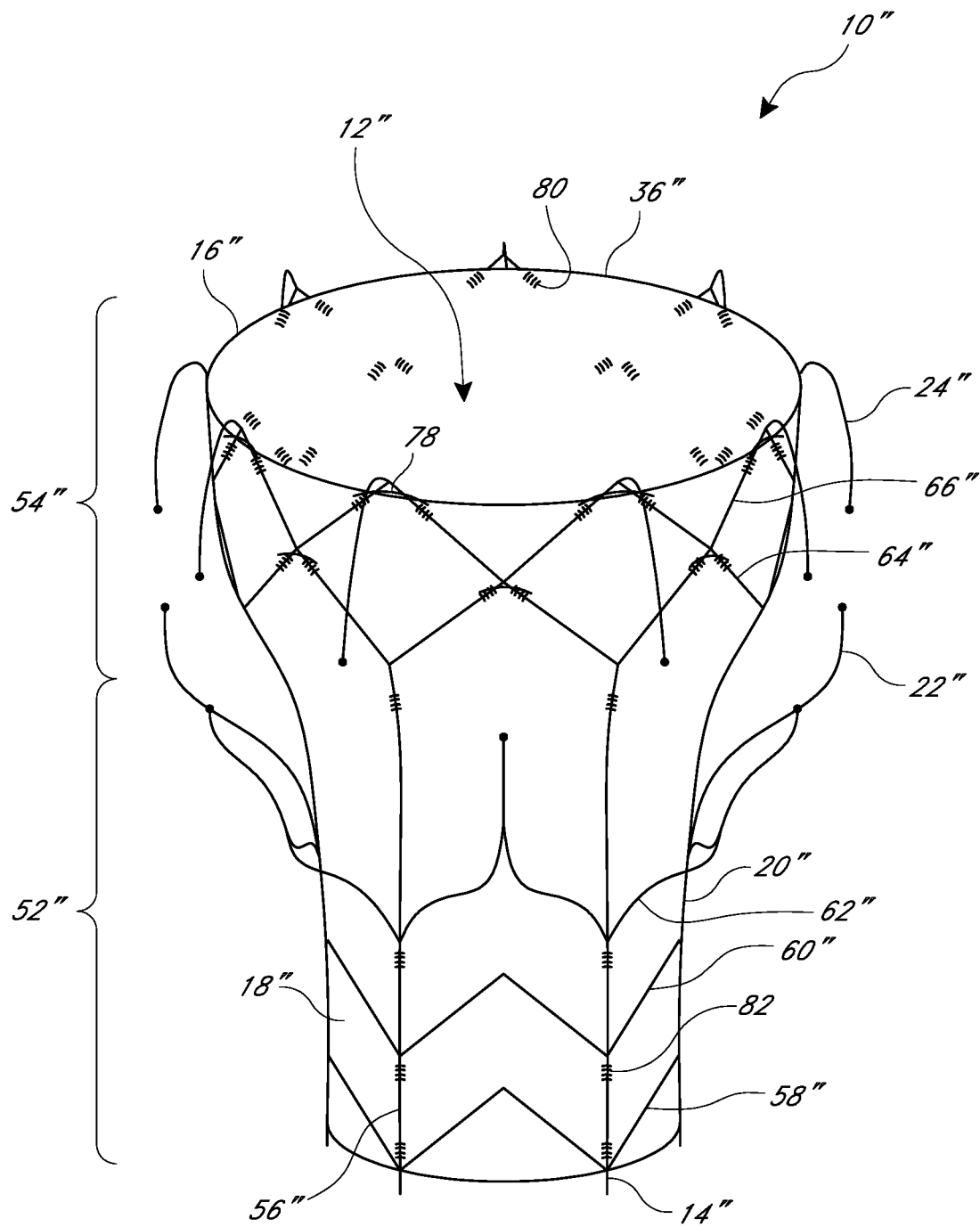
FIG. 5A is a perspective view of a replacement heart valve in an expanded state in accordance with an embodiment.
Figure 5B:
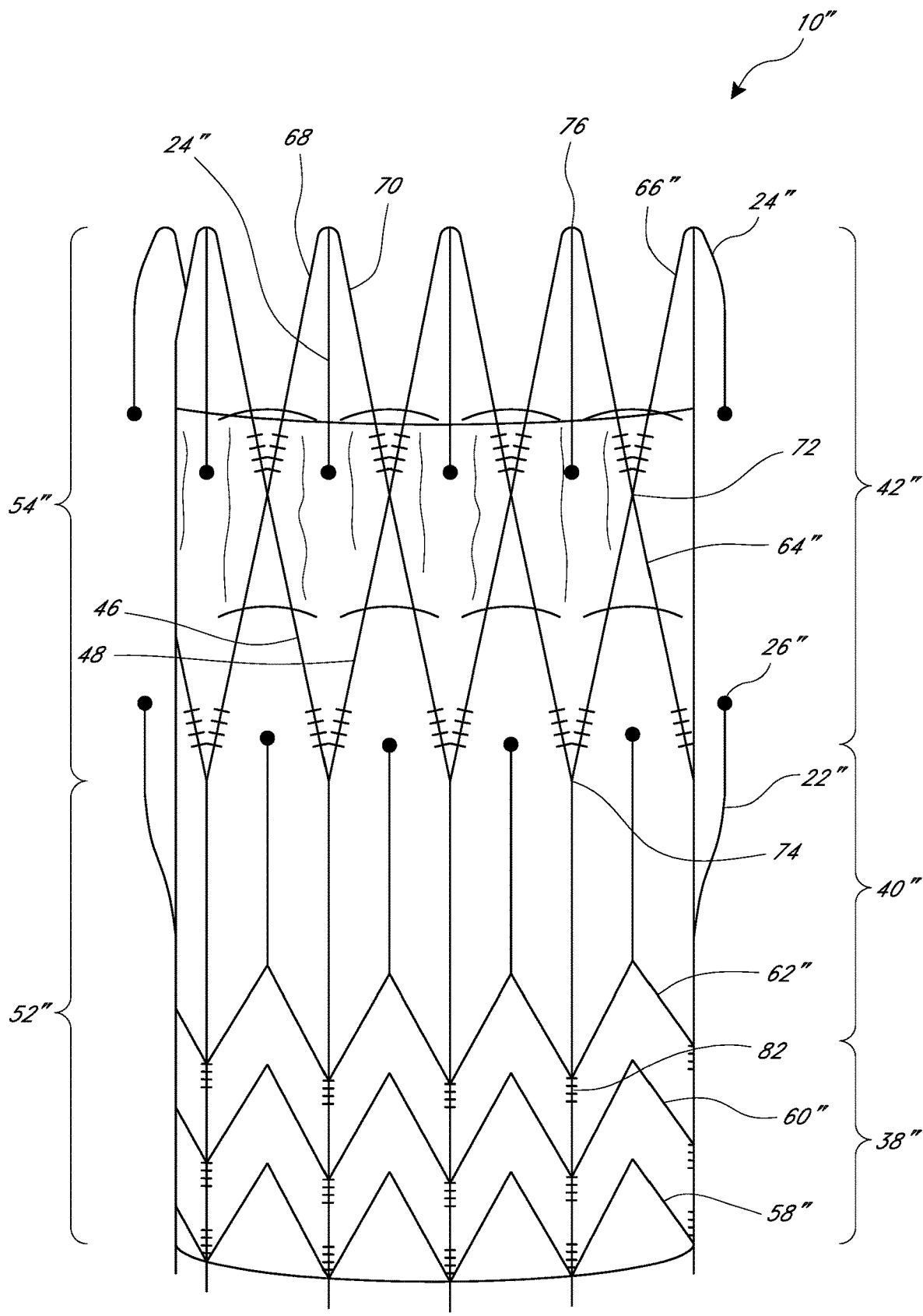
FIG. 5B is a side view of the replacement heart valve of FIG. 5A in a compacted state.

The replacement heart valve 10" generally has two configurations, an expanded state shown in FIG. 5A and a compacted state shown in FIG. 5B. The replacement heart valve 10" is typically stored in the compacted state prior to usage. In addition, the replacement heart valve 10" is generally mounted onto a delivery device to assume the compacted state. The compacted state is preferably sufficiently small in diameter to fit into a catheter that will be used to advance the replacement heart valve 10" through the vasculature and access the heart for deployment.

The replacement heart valve 10" is generally deployed to assume the expanded state at a diseased or damage heart valve. Preferably the replacement heart valve 10" transitions from the compacted state to the expanded state by self-expansion of the frame 20". In some embodiments, the replacement heart valve 10" transitions from a compacted to an expanded state by expansion of the frame 20" by a dilator, such as a balloon, or the like. The transition may also be performed by the combination of a self-expanding frame and a dilator.

Expansion of the frame 20" is controlled, at least in part, by the longitudinal 56" and undulating struts that make up the frame. As mentioned previously, the replacement heart valve 10" has a non-foreshortening portion 52" and a foreshortening portion 54". These portions can be defined at least in part by the frame 20" and the positioning of various types of struts along the frame 20".

The illustrated upstream portion 38" of the frame 20" is also part of the non-foreshortening portion 52". Longitudinal struts 56" substantially confine or restrict the upstream portion 38" from changing length upon the radial expansion or compaction of the frame 20". The upstream portion 38" expands and compacts only in the radial direction. At least one ring 58" of undulating struts can be positioned in the upstream portion 38". Second and third rings 60", 62" are also shown. The at least one ring 58" of undulating struts can extend circumferentially in a zigzag formation around the frame. Each ring can have two or more struts positioned between adjacent longitudinal struts 56". This allows the struts of the ring, as well as the longitudinal struts 56" to move closer together, or farther apart, as the replacement heart valve 10" is respectively compacted, or expanded.

The longitudinal struts 56" can also extend into the transition portion 40" between the upstream portion 38" and the downstream portion 42". The transition portion 40" defines a transition from the smaller upstream diameter to the larger downstream diameter of the replacement heart valve 10" when in the expanded state. In the illustrated embodiment the longitudinal struts 56" flare radially outwardly in the transition portion 40". As such, the frame 20" is generally divided into the upstream portion 38" made up of the first diameter, the transition portion 40" at which the diameter is expanding, and the downstream portion 42" with the larger second diameter.

The downstream portion 42" can also include at least one ring 64" of undulating struts. As shown in FIGS. 5A and 5B, the frame 20" has two rings 64" and 66" that form substantially diamond- or oval-shaped cells. FIG. 5A illustrates nine cells disposed circumferentially about the frame 20"; however, any quantity of cells can be implemented in the frame.

Each illustrated cell has two downstream struts 46, 48 and two upstream struts 68, 70. The individual cells are coupled to one another at junctions 72 located where one downstream strut 48 and one upstream strut 70 of one cell meet with one downstream strut 46 and one upstream strut 68 of another adjoining cell. The downstream undulating struts 46, 48 join to form downstream apex 74. The upstream undulating struts 68, 70 join to form upstream apex 76.

These diamond- or oval-shaped cells formed by the fourth 64" and fifth 66" rings in the downstream portion 42" longitudinally expand when the frame is radially compacted and longitudinally shorten when the frame is radially expanded as can be seen in FIGS. 5C-5D. In the compacted state of FIG. 5C, the junctions 72 are closer together than when in the expanded state shown in FIG. 5D. The longitudinally opposing apices 74, 76 are closest in the expanded state.

Thus, the fourth 64" and fifth 66" rings can make up the foreshortening zone 54". Expansion of the replacement heart valve 10" causes the struts of the fourth ring 64" to move angularly farther apart such that they are at a greater angle relative to one another. Thus, they move from a relatively vertical orientation to a more horizontal orientation. This also causes the ring 64" to shrink in vertical height. The fifth ring exhibits similar behavior when the valve 10" expands. This movement of the fourth 64" and fifth 66" rings results in foreshortening of the frame 20". It is to be understood that foreshortening can also be achieved with more or less rings of undulating struts, as well as with other configurations of the frame.

The positioning of the outer valve skirt 18", plurality of leaflets 12" and/or other components of the valve body within and along the frame 20", as well as the materials of the different parts of the replacement heart valve 10" can also affect how much expansion, compression, and/or foreshortening the replacement heart valve 10" can experience. In addition, the frame, the components of the valve body, and/or the connection(s) between the components of the valve body and the frame can be configured to deal with differences in material properties such as elasticity, and stretchability between the frame and the components of the valve body. It should be clear that some of these differences can be considerations for dealing with the foreshortening, non-foreshortening, expansion, and compaction of the replacement heart valve 10".

The outer valve skirt and leaflets are preferably made from tissue, such as pericardium. Pericardium, like some other suitable valve skirt materials, is flexible but not particularly stretchable or otherwise elastic. At the same time, the outer valve skirt and leaflets can be made to accommodate and substantially correspond to the shape of the frame in the expanded configuration.

In some embodiments of replacement heart valve 10, such as that shown in FIGS. 1-3, a connection skirt 50 can be connected to the downstream end 36 of the outer valve skirt 18. The connection skirt 50 can be made of an elastic fabric and can typically be placed to correspond to the foreshortening portion 52 of the frame 20. In this way, the connecting skirt 50 can stretch or compact with the longitudinal lengthening and shortening incident to radially compacting and expanding the valve 10. In such embodiments, the downstream end 36 of the pericardium valve skirt 18 can be connected to the connection skirt 50 at a circumferentially-extending seam.

Applicants have found that a circumferential seam can bunch up when the replacement heart valve 10 is compacted, thus limiting compaction of the valve. FIGS. 5A-5D illustrate an embodiment of replacement heart valve 10" without any circumferential seams. This enables the replacement heart valve 10" to be able to radially compact to a smaller diameter.

In the illustrated embodiment the outer valve skirt 18" is fabricated from one, two, three, or more longitudinally oriented pieces of tissue material, e.g., pericardium, or the like, that longitudinally span the frame length from the upstream end 14" to the downstream end 16". Preferably such longitudinal strips are stitched together by longitudinally-extending seams. Such construction lends itself to making the outer valve skirt 18" out of a single material and eliminates a circumferential stitch or seam joining sections of different materials. Thus, as mentioned, in the illustrated embodiment, there is no circumferential stitch or other such connections to the valve skirt.

In the illustrated embodiment, the outer valve skirt 18" is constructed of pericardium, which, like some other suitable valve skirt materials, is flexible but not particularly stretchable or otherwise elastic. Also, preferably the outer valve skirt 18" is stitched to the expanded-configuration frame 20" so that the downstream end 36" of the outer valve skirt 18" is generally or nearly coextensive with the downstream end 16" of the frame 20".

However, as noted above, when the implant is radially compacted, the longitudinal length of the frame 20" increases. As such, preferably the downstream portion of the outer valve skirt 18" is attached to the frame 20" in a manner that enables the frame 20" to move relative to the outer valve skirt 18". In this manner, when the foreshortening portion 54" increases in length, the outer valve skirt 18" can remain substantially the same length, but the struts of the foreshortening cells can move relative to the outer valve skirt 18". In this way, the outer valve skirt material is not substantially stretched or damaged.

In a preferred embodiment, the outer valve skirt 18" is attached to the non-foreshortening portion 52" of the frame 20" in a manner so that there is little to no relative longitudinal movement between the frame 20" and the outer valve skirt 18". The outer valve skirt 18" can be attached to the frame with a number of fasteners. The fasteners can be any device that can secure two objects together and can include two or more different types or different styles of device. Some example fasteners include stitches, staples, rivets, etc. Generally in the embodiments shown herein, stitches are used to attach the outer valve skirt to the frame, as well as to attach other components to one another. It will be understood that these are simply example fasteners and other devices could also be used.

FIGS. 5A-5D illustrate a stitching arrangement in which the outer valve skirt 18" is mounted to the frame 20" at the downstream portion so as to allow some relative movement. The downstream portion of the outer valve skirt 18" is mounted to the frame in the foreshortening portion 54" with loose or semi-loose stitching 78, 80 that allows the outer valve skirt 18" to slide relative to the frame struts 46, 48, 68, 70. At the other end, on the upstream portion the outer valve skirt 18" can be mounted to the frame 20" with tight stitches 82, which are stitches or other fasteners that are configured to substantially prevent longitudinal movement of the outer valve skirt 18" relative to the frame 20" in the non-foreshortening portion 52".

The tight stitches 82 can be tightly looped and/or cross-stitched around the struts 56" and through the outer valve skirt 18". The tight stitches 82 can be disposed about the longitudinal struts 56" at selective locations. As shown in FIGS. 5A and 5B, tight stitches 82 are positioned on the longitudinal struts 56" adjacent the apices of the first ring 58" on the downstream side of the connected apices. This prevents the tight stitches 82 from migrating off of the upstream end of the frame 20". Tight stitches 82 are also positioned adjacent the second 60" and third 62" rings on the upstream side of the connected apices, preventing the tight stitches 82 from migrating toward the downstream end of the replacement heart valve 10".

Other arrangements are also contemplated. For example, in some embodiments, tight stitches 82 can be located on both the upstream and downstream sides of the connected apices to prevent longitudinal migration of the outer valve skirt 18". In some embodiments, the tight stitches 82 can be looped through eyelets coupled to the upstream end of the longitudinal struts 56" and/or selectively located along the longitudinal struts. In still further embodiments, the tight stitches 82 can extend along, or span, a portion and/or the full length of one or more of the longitudinal struts 56".

Loose stitches 78, 80 can be used to allow some relative movement between the outer valve skirt 18" and the frame 20" as best seen in FIGS. 5C and 5D. The loose stitches can come in two types, those 80 that connect the outer valve skirt 18" to one strut and those 78 that connect the outer valve skirt 18" to two struts. A single strut stitch 80 loops around a single strut to couple the outer valve skirt 18" to the frame 20". A double-strut stitch 78 loosely loops around a pair of struts near the junction 72 when in the expanded state. The double-strut stitch 78 passes through the center of radially adjacent cells and the outer valve skirt tissue material.

The loose stitches 78, 80 have a greater distance between their respective points of entry into the outer valve skirt 18" tissue material than the tight stitches 82. The loose stitches 78, 80 also provide more room or space for strut movement relative to the outer valve skirt 18". The loose stitches 78, 80 readily allow the outer valve skirt 18" downstream end to float, or slide, relative to the frame 20", yet also sufficiently and durably mount the outer valve skirt 18" to the frame 20". In some embodiments, stitches that may not be physically loose-fitting may be placed so as to allow the outer valve skirt downstream end to float, or slide, relative to the frame. Such stitches, as well as physically loose stitches, can also be referred to as floating stitches or sliding stitches.

The loose stitches 78, 80 can allow the outer valve skirt 18" that is longitudinally shorter than the compacted frame to slide on the cell struts as the cells foreshorten during radial expansion, as illustrated in the detail views of FIGS. 5C and 5D. Four struts 46, 48, 68, 70 joined at each junction 72 radially expand from a compacted configuration in which the apices 74, 76 are relatively close to one another to an expanded configuration in which the apices 74, 76 are relatively farther apart. The loose stitches 78, 80 are urged downstream as the cells radially expand positioning the junctions 72 farther apart.

The double-strut stitch 78 is urged downstream because the distance between the apices 74, 76 and the upstream portions of the struts becomes wider than the stitch width and the stitch is urged toward the narrower portion of the V- or X-shaped configuration. This can be seen by comparing the position of the double-strut stitch 78 in FIG. 5D with that of FIG. 5C. The loose stitches "ride" the struts downstream to their final longitudinal position, as indicated by the arrows. The single stitch 80 also moves along the strut because of the movement of the double-strut stitch 78 and the outer valve skirt.

The positions of the loose stitches 78, 80 can be limited by the position of either or both of the junction 72 and the apices 74, 76. For example, in FIG. 5C, the stitches 78, 80 cannot pass any lower than the junction 72 and/or apices 74 of which they are positioned next to. To position the loose stitches 78, 80 lower than the junction 72 and/or apices 74, with the loose stitches 78, 80 still being around a strut would overload the stitch upon expansion because the lengthening of the frame would force the stitch downstream into the junction or apex.

Figure 6A:
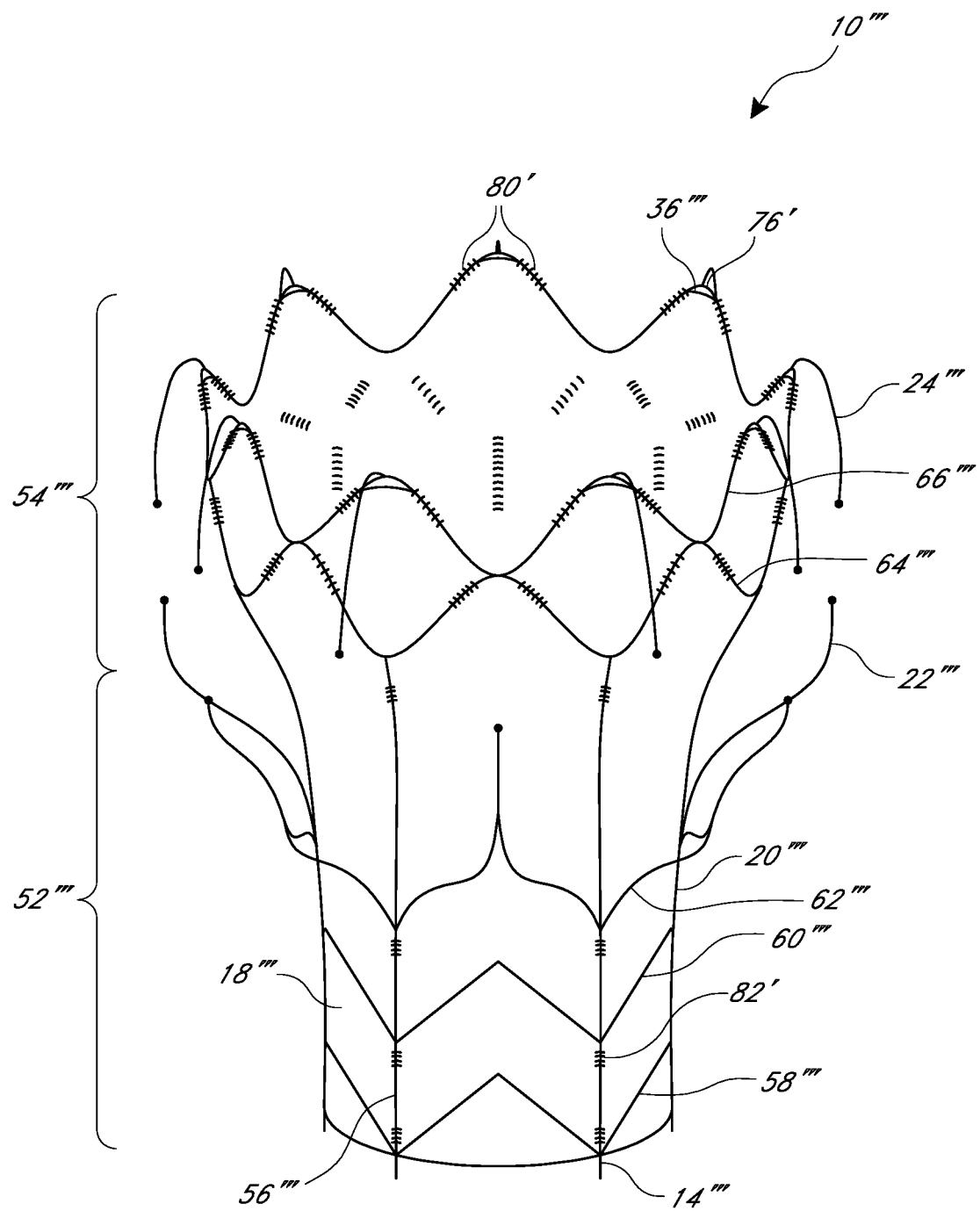
FIG. 6A is a perspective view of a replacement heart valve in an expanded state in accordance with an embodiment.
Figure 6B:
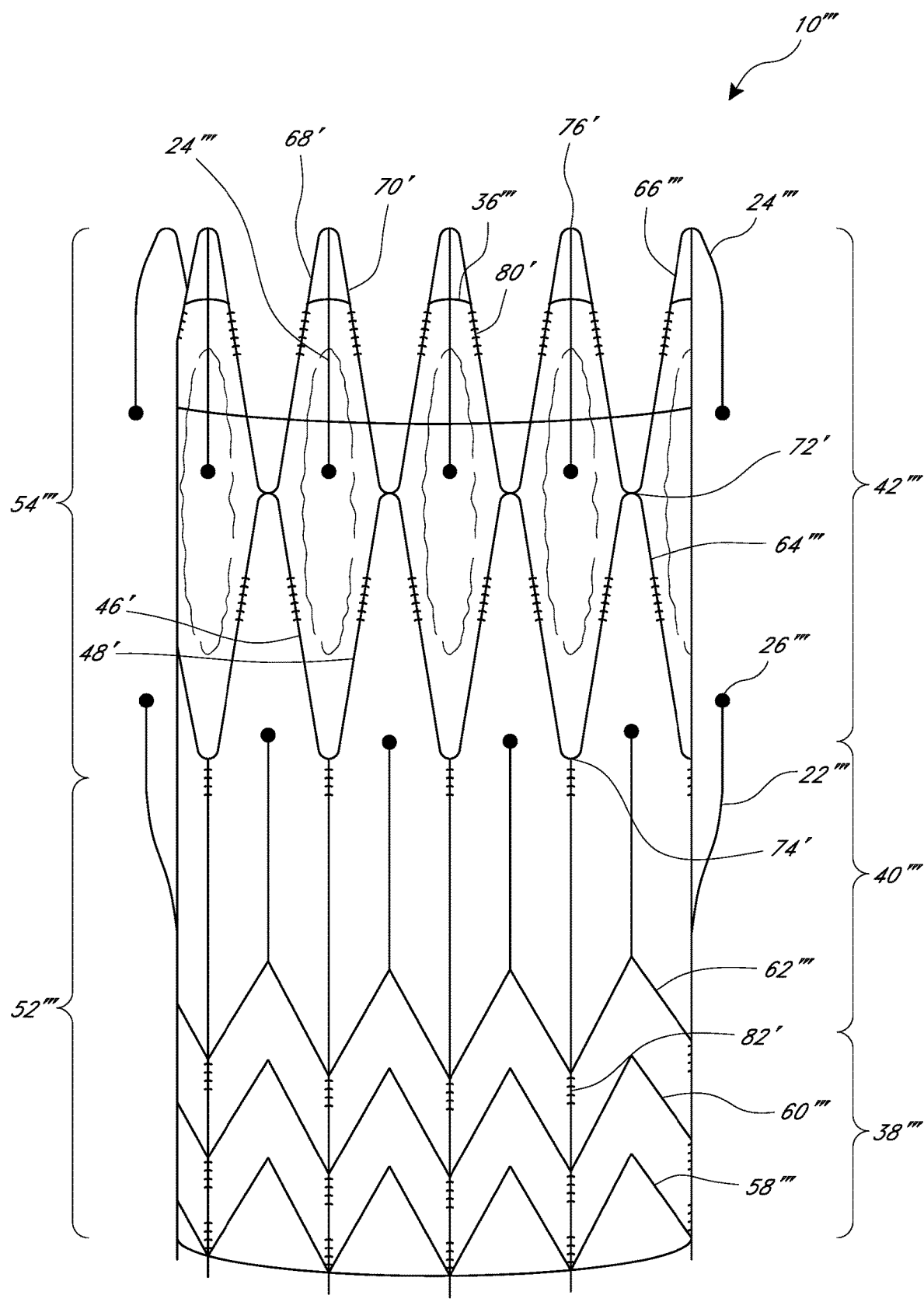
FIG. 6B is a side view of the replacement heart valve of FIG. 6A in a compacted state.

With reference now to FIGS. 6A and 6B, in another embodiment of replacement heart valve 10''', the downstream end of the outer valve skirt 18''' is connected to the struts in the downstream portion 42''' by multiple stitches 80'. In this embodiment, the downstream end 36''' of the outer valve skirt 18''' is shaped to correspond to the undulating pattern of ring 66''' when in the expanded state. However, as shown in FIG. 6A, the skirt is not attached to the downstream apices 76' and is spaced therefrom. As such, when the replacement heart valve 10''' is compacted, the outer valve skirt 18''' and stitches 80' will slide upstream relative to the downstream struts, resulting in a longitudinal space between the outer valve skirt distal end 36''' and the distal apices 76'. When the foreshortening cell is compacted, the cell longitudinal length increases but the outer valve skirt length does not, resulting in a longitudinal space between the downstream apex 76' and the downstream end 36''' of the outer valve skirt 18'''. The frame 20''' thus longitudinally expands while the outer valve skirt 18''' maintains its length.

Figure 7A:
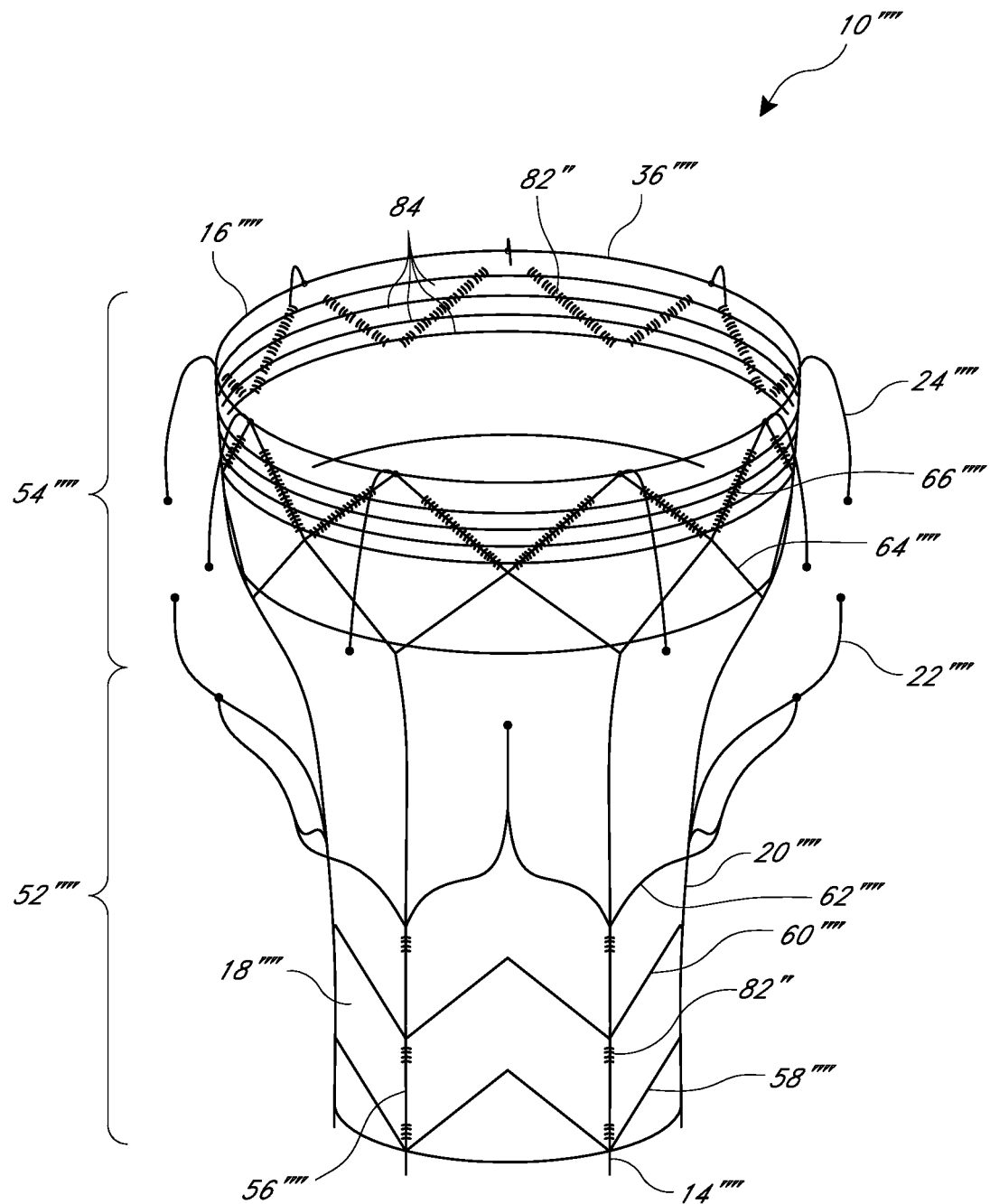
FIG. 7A is a perspective view of a replacement heart valve in an expanded state in accordance with another embodiment.
Figure 7B:
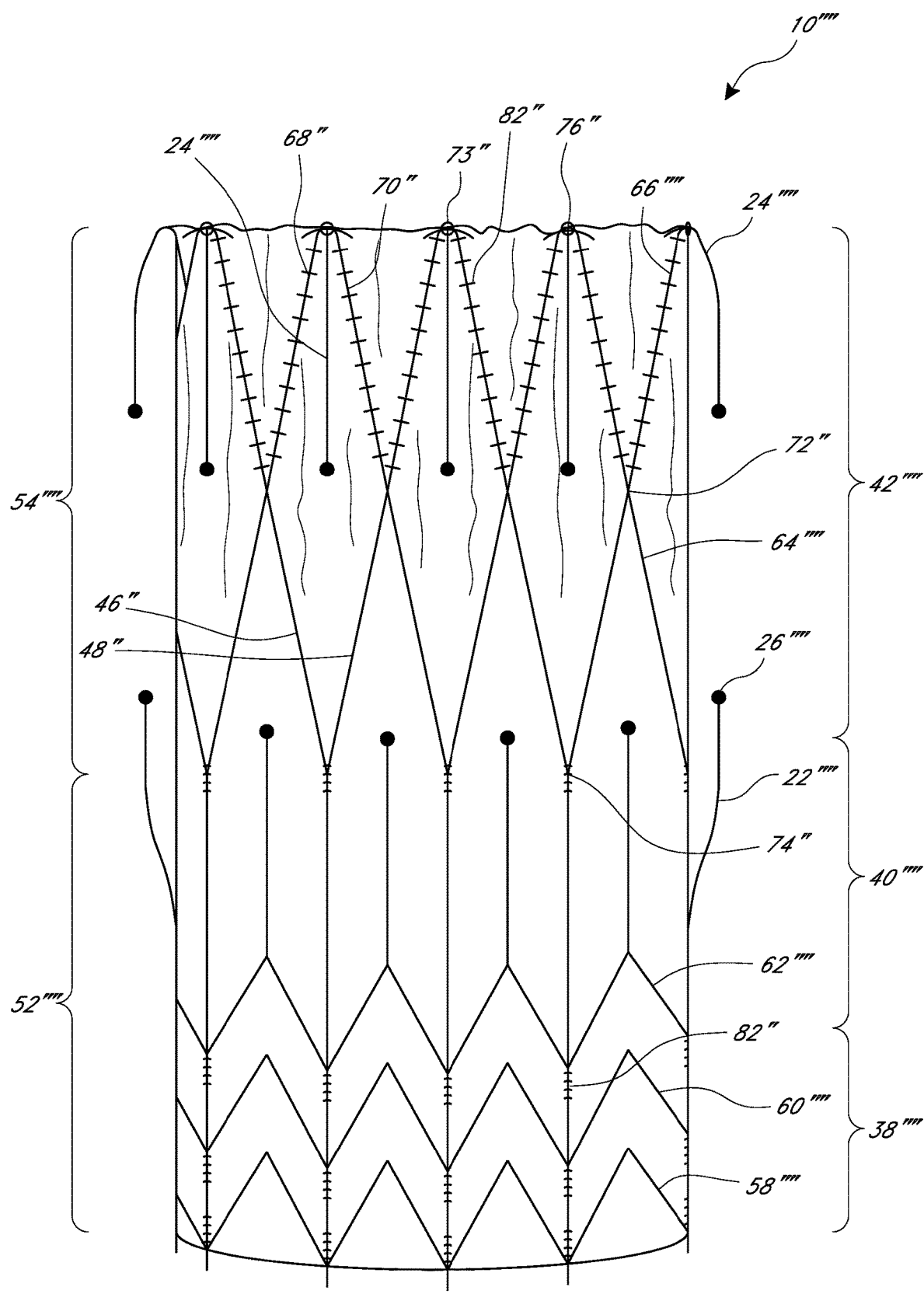
FIG. 7B is a side view of the replacement heart valve of FIG. 7A in a compacted state.
Figure 7C:
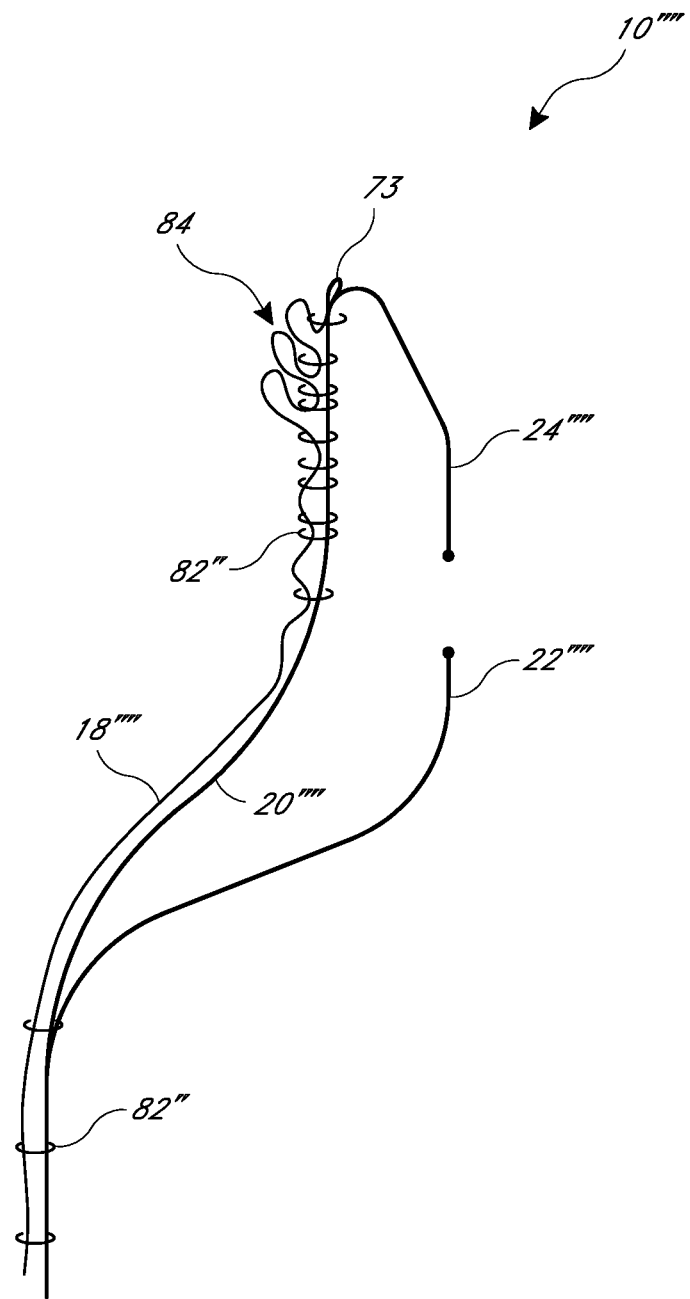
FIG. 7C is a cross-section side view of a portion of the expanded-state replacement heart valve of FIG. 7A.

FIGS. 7A-C illustrate still another embodiment of replacement heart valve 10'''', in which the longitudinal length of the outer valve skirt 18'''' skirt is generally the same, or substantially the same, as the longitudinal length of the frame 20'''' in the radially-compacted configuration. In this embodiment, tight stitches 82'' can be used in the both the non-foreshortening portion 52'''' and the foreshortening portion 54''''. The long outer valve skirt 18'''' configuration preferably extends from the compacted frame upstream end to the compacted frame downstream end. The outer valve skirt 18'''' downstream end 36'''' can be securely coupled, or stitched, to the frame downstream end 16'''' in a manner that the outer valve skirt 18'''' will substantially move with the frame 20'''' as the frame longitudinally expands and contracts.

The outer valve skirt 18'''' can be greater in length than the length of the expanded-state frame and substantially the same length as the compact frame. This can result in excess outer valve skirt material when the replacement heart valve is in the expanded configuration. The excess length of the outer valve skirt 18'''' can create circumferential folds 84, or material bunching, in the foreshortening portion of the frame, as depicted in FIGS. 7A and 7C.

FIG. 7C illustrates a cross-section side view of the implant tissue material in this embodiment positioned in the frame downstream end after the frame expands radially outward. Preferably the folding or bunching pattern can be selectively controlled by placement of stitches such as stitches at the junction 72''. It should be understood that, in other embodiments, the valve skirt can be shorter, longer, or any length therebetween, than the illustrated long configuration. A longer skirt than the long configuration skirt of FIG. 7C creates a greater number and/or size of circumferential folds.

Also illustrated in FIGS. 7A-7C are eyelets 73. The eyelets 73 can be used to attach to the outer valve skirt to the frame. In some embodiments, the downstream anchors 24'''' can be passed through the eyelets 73 when assembling the replacement heart valve 10''''. Stitching can also pass through the eyelets 73. The eyelets 73 can also reinforce the skirt material.

With continued reference to FIG. 7C, when the replacement heart valve 10'''' is installed in the body, the folds 84 in the valve skirt material preferably are positioned at or adjacent the native valve annulus. Thus, over time the folds can support tissue ingrowth, further securing the replacement heart valve 10'''' to the mitral valve native annulus and preventing leakage past the outer valve skirt 18''''.

Delivery Device and Method

Figure 8:
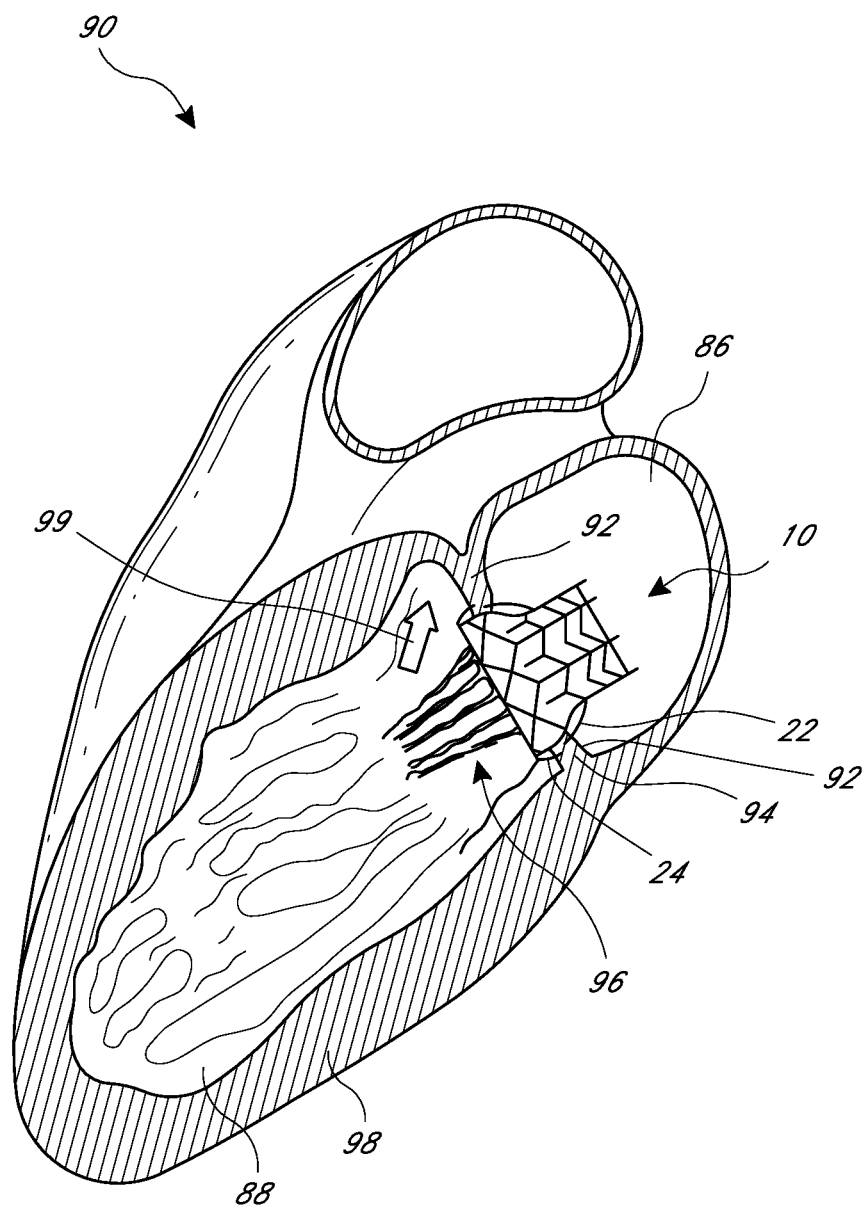
FIG. 8 schematically shows a replacement heart valve as in FIGS. 1-2 deployed in a native mitral annulus of a human heart.

With reference next to FIG. 8, a schematic representation of the replacement heart valve 10 as discussed above in connection with FIGS. 1 and 2 is depicted installed in a human heart 90. The heart is shown in cross-section, and represents typical anatomy, including a left atrium 86 and left ventricle 88. The left ventricle 88 is defined by a muscular wall 98. The left atrium 86 and left ventricle 88 communicate with one another through a mitral annulus 92. Also shown schematically in FIG. 8 is a native anterior mitral leaflet 94 having chordae tendineae 96 that connect a downstream end of the anterior mitral leaflet 94 to the muscle wall 98 of the left ventricle 88. A left ventricle outflow tract 99 extends toward the top of the left ventricle 88.

As shown, the replacement heart valve 10 is disposed so that the mitral annulus 92 is grasped between the upstream anchors 22 and the downstream anchors 24. As such, all or most of the replacement heart valve 10 extends into the left atrium 86. The portion of the replacement heart valve 10 disposed upstream of the annulus 92 can be referred to as being positioned supra-annularly. The portion generally within the annulus 92 is referred to as positioned intra-annularly. The portion downstream of the annulus is referred to as being positioned sub-annularly. In the illustrated embodiment, only a part of the foreshortening portion is positioned intra-annularly or sub-annularly, and the rest of the replacement heart valve 10 is supra-annular.

The following is an example of how the replacement heart valve 10 can be deployed at a patient's native mitral valve annulus with reference to FIG. 8. A radially-compacted replacement heart valve 10 is advanced on a delivery device through and past the mitral valve annulus 92 so that the downstream anchors 24 are positioned downstream of the native mitral valve leaflets 94. The heart valve 10 can be partially deployed so that the downstream portion of the replacement heart valve 10 can be allowed to self-expand, thus urging the downstream anchors 24 between the chordae tendineae 96 and radially outboard of the native mitral valve leaflets 94. The delivery device and replacement heart valve 10 can then be proximally retracted or moved upstream to engage the downstream anchors 24 with the downstream side of the native mitral valve annulus 92. In this motion, preferably the downstream anchors 24 engage and capture the native leaflets 94. Once the native leaflets are engaged and captured by the anchors 24, the remainder of the replacement heart valve 10 can then be deployed to allow self-expansion of the replacement heart valve 10 so that the upstream anchors 22 engage the upstream side of the native annulus 92, and the replacement heart valve 10 is deployed in operational condition. In some embodiments the replacement heart valve may not be self expanding, and the partial and full deployment may be accomplished by one or more inflatable balloons or the like.

Replacement heart valves can be delivered to a patient's heart mitral valve annulus in various ways, such as by open surgery, minimally-invasive surgery, and percutaneous or transcatheter delivery through the patient's vasculature.

Figure 9A:
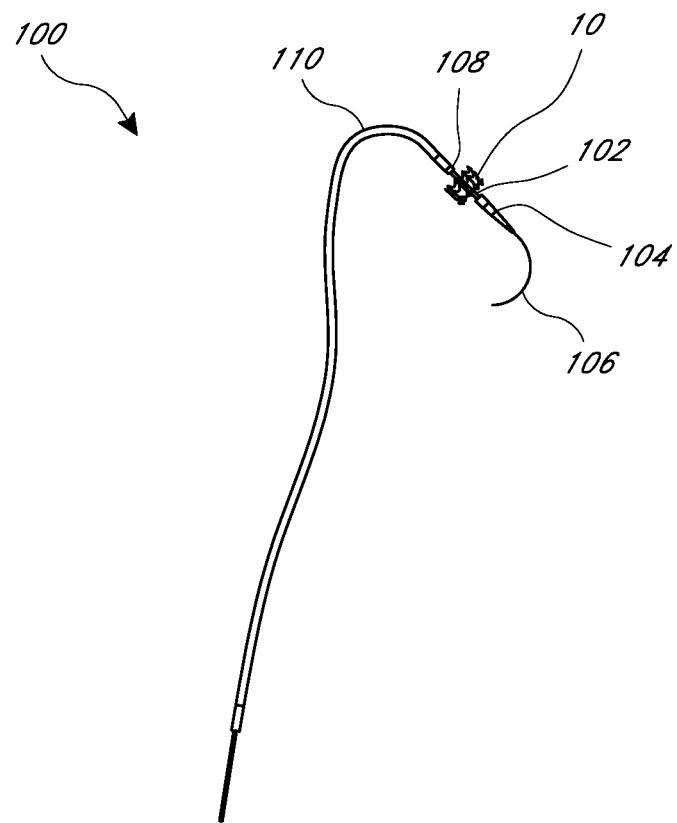
FIG. 9A shows an embodiment of a delivery device for delivering a replacement heart valve in accordance with one embodiment.
Figure 9B:
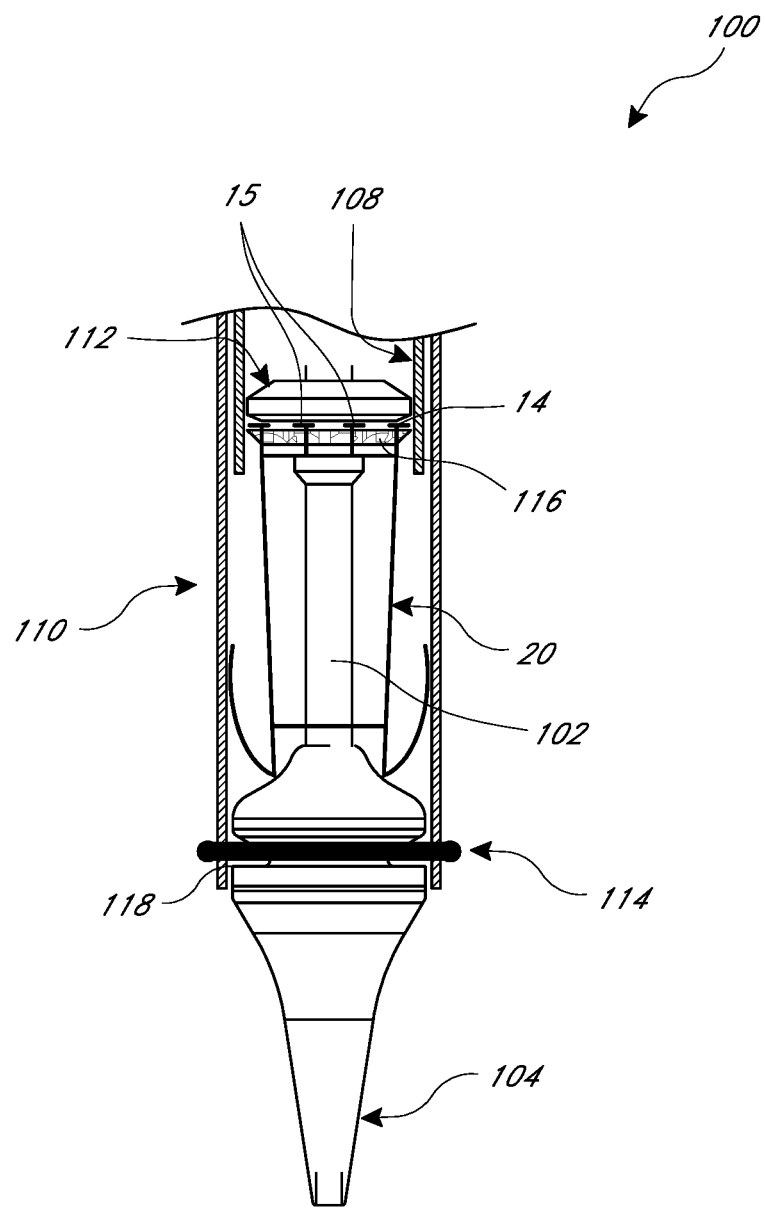
FIG. 9B shows a distal portion of the delivery device of FIG. 9A with a schematic representation of a valve frame.

With reference to FIGS. 9A-B, an embodiment of a delivery device 100 is shown in connection with a replacement heart valve 10. The illustrated embodiment comprises an elongate, delivery catheter configured to be advanced through a patient's vasculature in a percutaneous delivery approach. The delivery device 100 can be a spring or a cut metal hypotube that imparts rigidity to the device and yet allows flexibility to be able to pass through the curvosities of the vasculature. The delivery device 100 can also be covered with a polymer outer sheath.

The illustrated delivery device 100 comprises an elongate inner tube 102 that is attached at its distal end to a nose cone 104. The inner tube 102 has a lumen sized and configured to slidably accommodate a guidewire 106 so that the delivery device 100 can be advanced over the guidewire through the vasculature. The delivery device 100 may also be a steerable catheter which may or may not use a guidewire.

As can best be seen in FIG. 9B, an inner retention ring 112 can be positioned on the inner tube 102. A support tube or outer retention ring 108 concentrically encircles the inner tube 102 and is sized to be slidable over the inner tube and the inner retention ring. In the illustrated embodiment the support tube is elongate. An outer sheath 110 is disposed so as to be slidable over the support tube 108.

In the illustrated embodiment, and preferably, in a manner as discussed in embodiments presented below, the support tube or outer retention ring 108 and outer sheath 110 cooperate to grasp onto the replacement heart valve 10. FIG. 9B schematically shows a valve frame 20 within and secured by the outer sheath 110 and other components of the delivery device 100. The inner retention ring 112 is also shown engaging the proximal end 14 of the valve frame 20. For example, teeth 116 on the inner retention ring 112 can engage tabs 15 on the proximal end 14 of the valve frame 20. The outer retention ring 108 can be positioned over the inner retention ring 112 so that the proximal end of the replacement heart valve 10 is trapped therebetween, securely attaching it to the delivery device 100.

The outer sheath 110 can also be positioned over the distal end of the delivery device 100 and over the replacement heart valve 10. As shown, the outer sheath 110 is advanced over a portion of the nose cone 104 of the delivery device 100. Optionally, a retainer member 114, e.g., an o-ring, a clamp, a cover, or the like, can be used to retain the outer sheath 110 in place. As shown, an o-ring 114 is placed over the outer sheath 110 at a groove or slot 118 disposed circumferentially around the nose cone 104. In some embodiments, the nose cone can include a flange that encompasses and secures the outer sheath, so that the outer sheath fits into the nose cone under the flange. This flange may also cover all or part of the replacement heart valve. In some embodiments, the delivery device may include one or more additional sheaths or other features that can be advanced over all or part of the replacement heart valve.

The delivery device 100 is configured to retain and restrict the valve frame 20 and the replacement heart valve 10 from expanding. The delivery device 100 restrains the replacement heart valve 10 until the replacement heart valve 10 is deployed from the delivery device 100 at, or adjacent, the native mitral valve annulus 92.

Figure 10A:
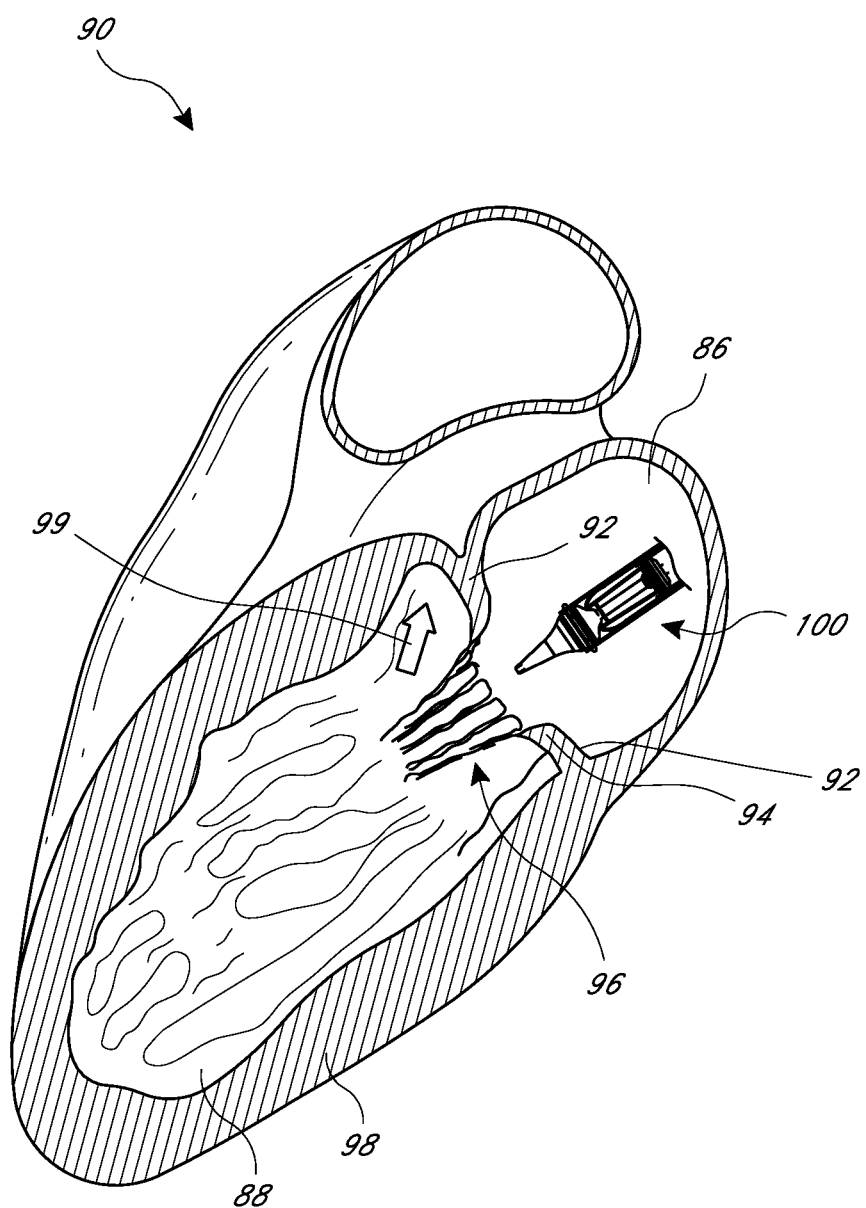
FIGS. 10A-C schematically show a replacement heart valve and steps of a method of deploying the replacement heart valve according to one embodiment.

With reference next to FIGS. 10A-10C and FIG. 8, an embodiment of a method and apparatus for deploying a replacement heart valve 10 is depicted. Referring to FIG. 10A, it can be seen that the replacement heart valve 10, mounted in a radially-compacted configuration on the distal end of the delivery device 100, is introduced into the left atrium 86 of the heart 90. As shown, the native mitral leaflets 94 (posterior leaflet shown) extend downstream of the native annulus 94, and chordae tendineae 96 extend downstream from the mitral valve to the ventricle wall.

Figure 10B:
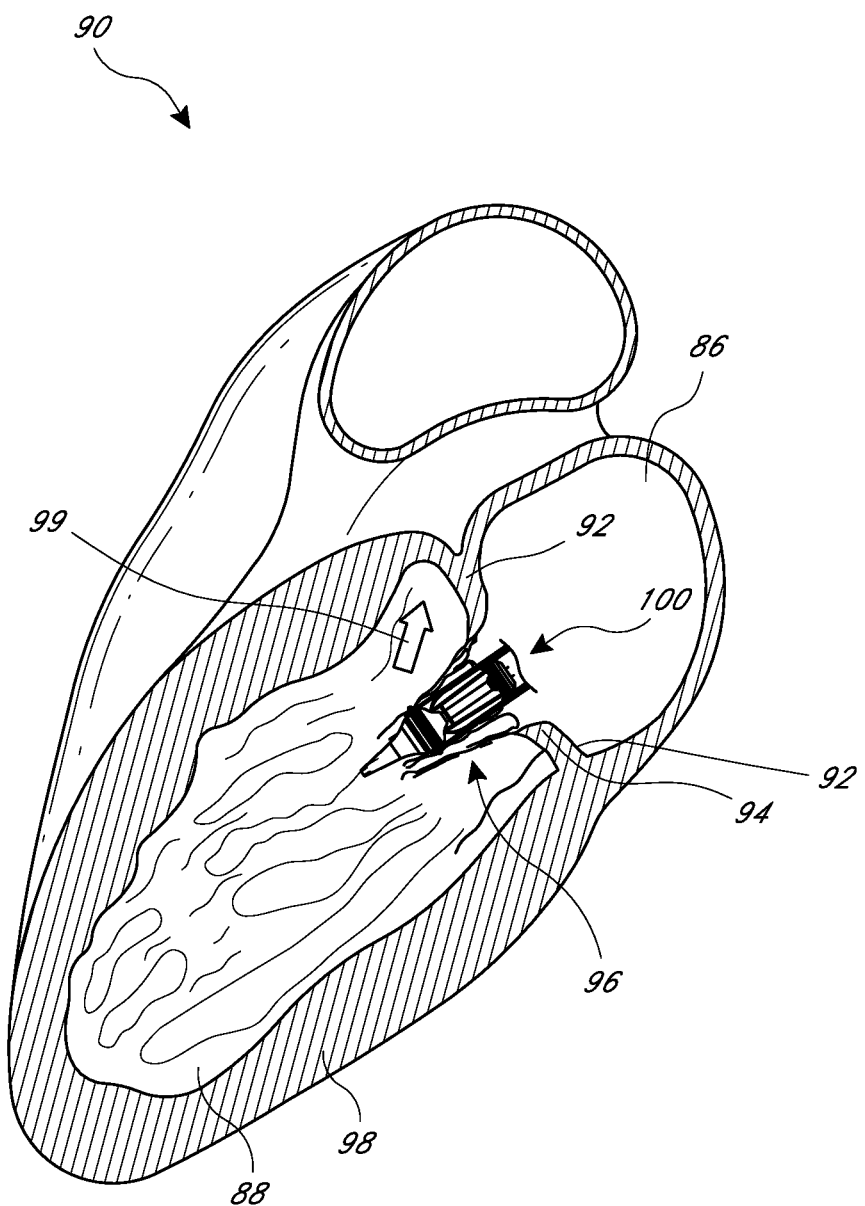

With reference next to FIG. 10B, the delivery device 100 is advanced so that the replacement heart valve 10 is positioned slightly downstream of its final mounting point. More specifically, it is positioned so that the downstream anchors 24 are positioned downstream of where the chordae tendineae 96 connect to the free end of the native mitral valve leaflets 94.

Figure 10C:
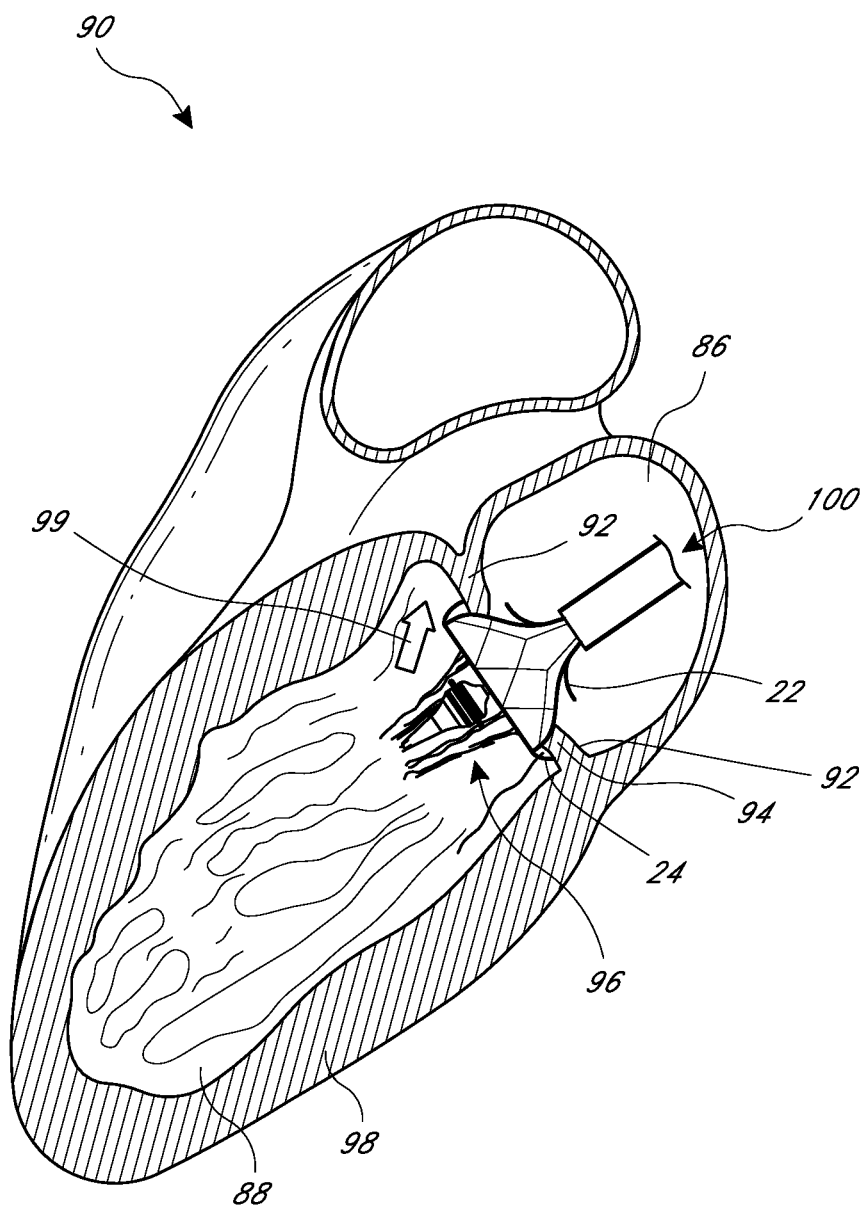

The outer sheath 110 is then at least partially retracted to expose at least part of the downstream end of the replacement heart valve 10, including the downstream anchors 24 as shown in FIG. 10C. The downstream end of the replacement heart valve 10 radially expands to approximately the full extent, or slightly less than the full extent. At the same time, the upstream end of the replacement heart valve 10 is still retained by the delivery device and is at least partially radially compacted. During expansion of the downstream end of the replacement heart valve 10 the downstream anchors 24 pass between chordae tendineae 96 so that the upstream-directed downstream anchor tips 28 substantially face the downstream side of the native mitral valve annulus 92. As the upstream portion of the replacement heart valve 10 is still retained by the delivery device 100 in a partially radially-compacted state, the position of the replacement heart valve 10 can still be readily adjusted.

After the downstream anchors 24 are expanded to be positioned downstream of and radially outside of the native leaflets 94, the delivery device 100 and replacement heart valve 10 are moved in an upstream direction. This causes the downstream anchors 24 and anchor tips 28 to engage with the downstream side of the native annulus 92, and the native leaflets 94. The native leaflets 94 are engaged and possibly retracted by the anchors. In some embodiments, the anchors pull the native leaflets 94 proximally, resulting in the native leaflets 94 being bunched up, and the chordae tendineae 96 being stretched and/or tightened. In other embodiments the native leaflets 94 may not be bunched up or may be only partially bunched up, but are contained by the anchors so as to prevent movement of the leaflets 94 into, for example, the left ventricle outflow tract 99.

Once the downstream anchors 24 are properly placed, the delivery device 100 can release the upstream anchors 22 and the remaining upstream end 14 of the replacement heart valve 10. This can be done by retracting the outer retention ring 108. In some embodiments this can be done by fully retracting the outer sheath 110, as well as, the outer retention ring 108.

As discussed previously, the upstream anchors 22 flare radially outward under the self-expansion force of the frame 20 and advance toward the upstream side of the native mitral valve annulus 92 under the foreshortening force of the cells. The downstream 24 and upstream 22 anchors can thus securely grasp the native mitral valve annulus 92 between their opposingly directed anchor tips, and the replacement heart valve 10 is fully and securely installed as can be seen in FIG. 8. The anchor placement can preferably prevent or reduce the prevalence of any up and/or down motion of the frame. The anchor placement can also help ensure that the replacement heart valve is perpendicular to the annulus and prevents any "rocking" and/or tilting of the frame. By engaging both the native annulus 92 and the native leaflets 94 by the frame 20 and anchors 22, 24 the load can be more evenly distributed to achieve equilibrium. Such a configuration can also provide a more robust implantation.

The independent nature of each anchor can allows the frame to conform to a number of different shapes. For example, the three dimensional annular shape of the mitral valve may not be entirely flat, and in fact, as is the case with most mitral anatomy, may be more saddle shaped. Thus, the independent anchors can stretch and bend to be able to engage these different shapes.

In embodiments in which the native leaflets 94 are compacted and urged against both the outer surface of the replacement heart valve 10 and the native annulus 92, the bunched up leaflets advantageously provides additional leak prevention between the native tissue and the replacement heart valve 10, or between the anchors and the valve frame.

Figure 11:
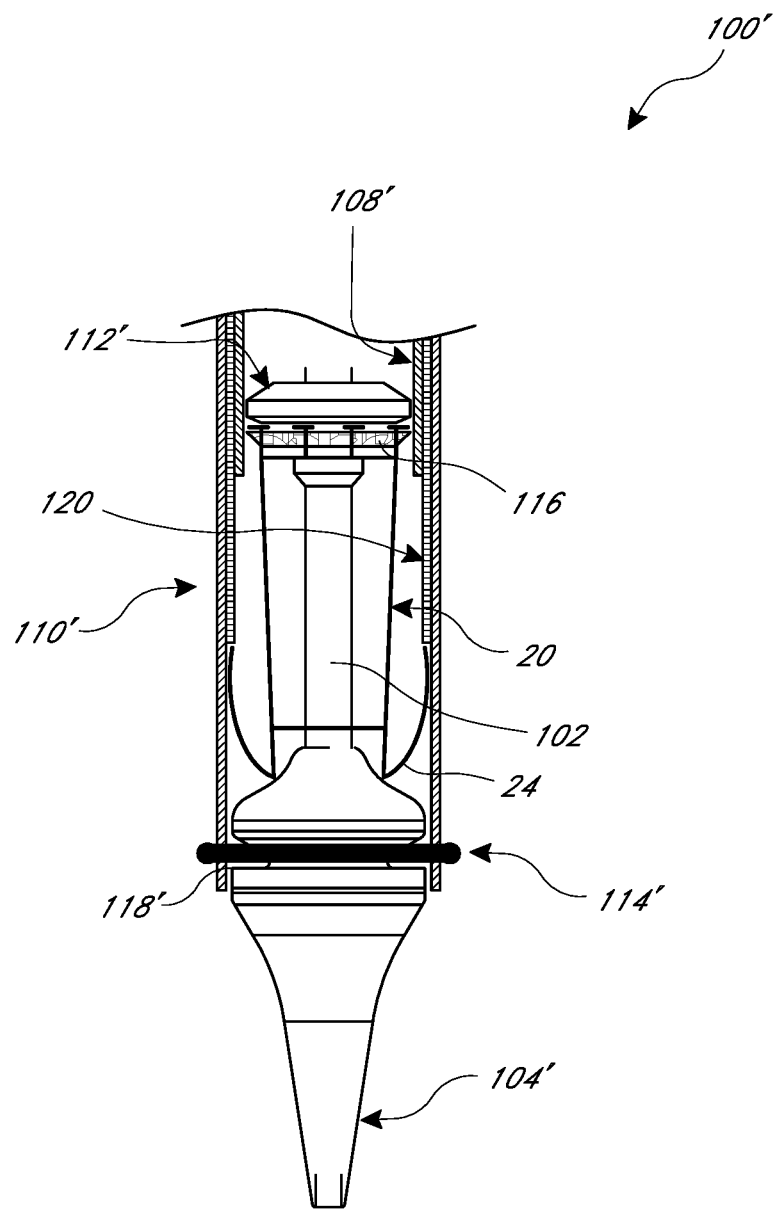
FIG. 11 shows a distal portion of another embodiment of delivery device with a schematic representation of a valve frame.

Referring now FIG. 11, another embodiment of delivery device 100' is shown. Numerical reference to components is the same as previously described, except that a prime symbol (') has been added to the reference. Where such references occur, it is to be understood that the components are the same or substantially similar to previously-described components. The illustrated embodiment comprises an elongate, delivery catheter configured to be advanced through a patient's vasculature in a percutaneous delivery approach. In addition to an outer sheath 110' and an outer retention ring 108', the delivery device 100' can also include a secondary sheath 120.

The secondary sheath 120 can be slidable over the outer retention ring 108' which is slidable over the inner tube 102' and the inner retention ring 112'. The outer sheath 110' is disposed so as to be slidable over both the support tube 108' and the secondary sheath 120. The outer retention ring 108', secondary sheath 120 and outer sheath 110' all cooperate to grasp onto the replacement heart valve 10. FIG. 11 schematically shows a valve frame 20 within and secured by these three components.

The secondary sheath 120 can be advanced over all or a part of the replacement heart valve 10. As such, the secondary sheath 120 can be used to further control the expansion of the replacement heart valve 10 during the delivery process. For example, the secondary sheath 120 can be positioned so that the distal end is right next to but not covering the downstream anchors 24. Thus, when the outer sheath 110' is withdrawn, the secondary sheath 120 can limit the expansion of the replacement heart valve 10. In some embodiments, the secondary sheath 120 can limit the expansion of the replacement heart valve 10 to just the downstream anchors 24 or just the downstream anchors and a small amount of radial expansion of the foreshortening cells.

In some embodiments, the secondary sheath 120 can be positioned at the base of the downstream anchors 24 such that the secondary sheath 120 is between the downstream anchors 24 and the rest of the frame 20. Thus, the secondary sheath 120 can cover the frame 20 essentially to the distal end 16, with primarily only the downstream anchors 24 exposed. Again, this can limit the expansion of the replacement heart valve 10 upon withdrawal of the outer sheath 110'.

The delivery methods described above with reference to delivery device 100 and FIGS. 10A-C can be considered a two stage delivery method; the first stage being withdrawal of the outer sheath 110, and the second stage being withdrawal of the outer retention ring 108. The delivery device 100' can use a three stage delivery method as will be described below. It should be understood that both delivery devices 100, 100' can also be used in other delivery methods that may be considered single stage, two stage, three stage, etc.

The delivery device 100' can be used in a delivery procedure similar to that described above. The delivery device 100' can have a replacement heart valve 10 mounted in a radially-compacted configuration on the distal end and be introduced into the left atrium 86 of the heart 90. The delivery device 100' can be advanced to position the replacement heart valve 10 slightly downstream of its final mounting point. More specifically, the replacement heart valve 10 can be positioned so that the downstream anchors 24 are positioned downstream of where the chordae tendineae 96 connect to the free end of the native mitral valve leaflets 94.

The outer sheath 110' can then be at least partially retracted to expose at least the downstream anchors 24. The secondary sheath 120 and outer retention ring 108' can still be positioned over the replacement heart valve 10 to limit expansion of the replacement heart valve 10 after withdrawal of the outer sheath 110.

With the downstream anchors 24 exposed and little to no other expansion experienced, the delivery device 100' can easily position the downstream anchors 24 in an initial desired position. The secondary sheath 120 can then be retracted allowing the replacement heart valve 10 to further expand while still being attached at the proximal end 14 to the delivery device 100' at the inner 112 and the outer 108 retention rings. The replacement heart valve 10 can then be adjusted again prior to completely releasing the replacement heart valve 10 from the delivery device 100'.

In some embodiments, the downstream anchors 24 can be positioned first next to one part of the native valve annulus before the secondary sheath 120 is withdrawn. As the mitral valve is a bicuspid valve, the delivery device 100' can be used to attach the downstream anchors 24 to one of the leaflets, such as the posterior leaflet and then to the other of the leaflets, such as the anterior leaflet. This second part can be done after the replacement heart valve 10 is expanded or further expanded by moving the secondary sheath 120. In some embodiments, staged deployment can also be achieved without the use of a secondary sheath. For example, a primary sheath with sufficient column strength and/or resistance to collapsing/corrugating/compression along the axis can be used to achieve staged deployment.

In some embodiments, the entrance route of the delivery device 100' into the left atrium 86 can bias the delivery device 100' towards one side of the mitral valve 92. For example, the delivery device 100' may be biased towards the posterior leaflet of the mitral valve 92. Also, an axis of the delivery device may be angled relative to an axis of the native annulus. This can facilitate securing the downstream anchors 24 to the posterior side or the posterior leaflet first, prior to expanding or further expanding the replacement heart valve 10. The downstream anchors 24 can then be secured to the anterior side of the mitral valve 92 or to the anterior leaflet.

For example, the downstream anchors 24 can be positioned initially past the mitral valve annulus 92 and then moved upstream to engage one side and/or one leaflet. The delivery device 100' can then be repositioned, or first the secondary sheath 120 removed then the delivery device 100' repositioned. The delivery device 100' can again be moved upstream, this time so that the downstream anchors 24 on the other side will also engage the other side of the mitral valve 92 and/or the other leaflet.

After the downstream anchors 24 are released the delivery device 100' and replacement heart valve 10 are moved in an upstream direction. This causes the downstream anchors 24 and anchor tips 28 to engage with the downstream side of the native annulus 92, and the native leaflets 94. The native leaflets 94 are engaged and possibly retracted by the anchors. As mentioned, this can occur first on one side or to one leaflet and then to the other side or to the other leaflet.

Once the downstream anchors 24 are properly placed, the delivery device 100' can then release the upstream anchors 22 and the remaining upstream end 14 of the replacement heart valve 10. This can be done by retracting the outer retention ring 108'. In some embodiments this can be done by retracting the outer retention ring 108' as well as fully retracting one or more of the outer sheath 110' and the secondary sheath 120.

As discussed previously, the upstream anchors 22 flare radially outward under the self-expansion force of the frame 20 and advance toward the upstream side of the native mitral valve annulus 92 under the foreshortening force of the cells as the cells complete their radial expansion. The downstream 24 and upstream 22 anchors thus securely grasp the native mitral valve annulus 92 between their opposingly directed anchor tips, and the replacement heart valve 10 is fully and securely installed as can be seen in FIG. 8.

Multi-stage release of the replacement heart valve 10 by the delivery device 100, 100' can facilitate better control and positioning of the replacement heart valve 10 at the native annulus 92. As explained above, three stage release by the delivery device 100' can allow for a quicker and more reliable securement of the replacement heart valve 10 to the mitral valve 92.

A delivery device 100, 100' with one or more of an outer sheath, a secondary sheath and/or an outer retention ring can control their movement in different ways. For example, each or some of the outer sheath, secondary sheath and outer retention ring can move separately and independently from the others. Alternatively, or in addition, some can be moved together, such as being attached to move in a coordinated fashion.

For example, the secondary sheath can be attached to the outer sheath through sutures, stitches, wire, string, cable, band, ribbon, etc. This can allow the outer sheath to be withdrawn initially without affecting the positioning of the secondary sheath. The outer sheath can then be further removed, causing tension on the secondary sheath through whichever device has been used to attach the two. Thus, the secondary sheath can be a floating sheath. In some embodiments, internal wires or outer coverings may extend the length or substantially the length of the delivery device and can be actuated at the proximal end.

In another embodiment, the outer sheath can be folded over itself in one or more positions to take the place of a secondary sheath and/or an outer retention ring. For example, the distal end of the outer sheath can be positioned over the inner retention member and then the outer sheath can be folded over itself to cover the replacement heart valve. Initial movement of the outer sheath can uncover a part of the replacement heart valve without uncovering the inner retention member.

In still another embodiment, the nose cone can be used to cover a portion of the replacement heart valve such as the downstream anchors. The nose cone can include a flange that encompasses and secures the outer sheath, so that the outer sheath fits into the nose cone under the flange. This flange may cover all or part of the replacement heart valve. The nose cone can be advanced exposing and expanding the anchors. The outer sheath can cover the rest of the device and can then be later withdrawn similar to the secondary sheath.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. For example, the support band can be used with the replacement heart valves shown in FIGS. 1-3, 5A-7C. Also, connection skirt can be used with the replacement heart valve shown in FIG. 4. Further, additional embodiments of valve delivery devices, whether or not disclosed herein, may employ, for example, the two and three-stage delivery methods discussed herein. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. An implantable prosthetic valve comprising:
    an annular frame comprising an upstream portion and a downstream portion and being radially collapsible and expandable between a radially collapsed configuration and a radially expanded configuration, wherein the frame comprises a plurality of struts;
    a leaflet structure positioned within the frame and secured thereto; and
    an outer skirt comprising a first portion that is tightly connected to the frame with first stitches such that the first portion is prevented from moving axially with respect to the frame when the frame radially expands and collapses and a second portion that is loosely connected to the frame with second stitches such that the second portion can move axially with respect to the frame when the frame radially expands and collapses, and wherein at least one of the second stitches is connected to two struts of the frame.

2. The prosthetic valve of claim 1, wherein the at least one of the second stitches is configured such that it slides along the two struts of the frame when the frame is radially expanded and collapsed.

3. The prosthetic valve of claim 1, wherein the frame comprises a plurality of undulating struts arranged in rings positioned along the length of the frame, and wherein the at least one of the second stitches is looped around two adjacent undulating struts of the same ring.

4. The prosthetic valve of claim 1, wherein the frame comprises a plurality of longitudinal struts and a plurality of undulating struts, and wherein at least one of the first stitches is connected to a longitudinal strut.

5. The prosthetic valve of claim 1, wherein at least one of the second stitches is connected to a single strut of the frame.

6. The prosthetic valve of claim 1, wherein at least one of the first stitches is connected to a single strut of the frame.

7. The prosthetic valve of claim 1, wherein the outer skirt comprises a non-stretchable material.

8. The prosthetic valve of claim 1, wherein the second stitches are configured such that they are forced to move in an axial direction relative to the frame when the frame radially expands.

9. The prosthetic valve of claim 1, wherein the first portion of the outer skirt comprises an upstream portion and the second portion of the outer skirt comprises a downstream portion.

10. An implantable prosthetic valve comprising:
an annular frame comprising an inflow end and an outflow end and being radially collapsible and expandable between a radially collapsed configuration and a radially expanded configuration;
a plurality of valve leaflets positioned within the frame and secured thereto; and
an outer skirt comprising a first portion that is secured to the frame such that the first portion is prevented from moving axially relative to the frame when the frame radially expands and collapses, the outer skirt further comprising a second portion axially spaced from the first portion along a length of the outer skirt, the second portion being loosely connected to the frame with stitches such that the second portion can move relative to the frame when the frame radially expands and collapses, and wherein at least one of the stitches is connected to two struts of the frame.

11. The prosthetic valve of claim 10, wherein the at least one of the stitches is configured to slide with the second portion of the outer skirt along the two struts of the frame when the frame is radially expanded and collapsed.

12. The prosthetic valve of claim 10, wherein the frame comprises a plurality of circumferentially extending rows of undulating struts, wherein the at least one of the stitches is looped around the two struts, wherein the two struts comprise two adjacent undulating struts of the same row.

13. The prosthetic valve of claim 10, wherein the first portion of the outer skirt is secured to the frame by tight stitches.

14. The prosthetic valve of claim 10, wherein another one of the stitches is connected to a single strut.

15. The prosthetic valve of claim 14, wherein the another one of the stitches forms multiple loops extending around the single strut and through the first portion of the outer skirt.

16. The prosthetic valve of claim 10, wherein the outer skirt comprises a non-stretchable material.

17. The prosthetic valve of claim 10, wherein the first portion of the outer skirt comprises an inflow end portion of the skirt and the second portion of the outer skirt comprises an outflow end portion.

18. An implantable prosthetic valve comprising:
an annular frame comprising an upstream portion and a downstream portion and being radially collapsible and expandable between a radially collapsed configuration and a radially expanded configuration, wherein the frame comprises a plurality of struts;
a leaflet structure positioned within the frame and secured thereto; and
an outer skirt comprising an upstream portion and a downstream portion, wherein the upstream portion is connected to the frame with first stitches such that the upstream portion of the outer skirt is prevented from moving axially with respect to the frame when the frame radially expands and collapses and the downstream portion is connected to a foreshortening portion of the frame with second stitches such that the downstream portion of the outer skirt can move axially with respect to the frame when the frame radially expands and collapses, and wherein at least one of the second stitches is connected to two struts of the frame that can slide axially relative to the two struts when the frame radially expands and collapses.

19. The prosthetic valve of claim 18, wherein the at least one of the second stitches loosely wraps around the two struts adjacent a junction between the two struts.

20. The prosthetic valve of claim 18, wherein at least one of the first stitches is connected to a single strut of the frame.

* * * * *